(12) United States Patent
Whitley et al.

(10) Patent No.: US 7,592,321 B2
(45) Date of Patent: Sep. 22, 2009

(54) METHODS OF TREATING LYSOSOMAL STORAGE RELATED DISEASES BY GENE THERAPY

(76) Inventors: Chester B. Whitley, 8837 Stratford Crossing, Brooklyn Park, MN (US) 55443; R. Scott McIvor, 3745 Glenhurst Ave., South, St. Louis Park, MN (US) 55416

(*) Notice: Subject to any disclaimer, the term of this patent is extended or adjusted under 35 U.S.C. 154(b) by 79 days.

(21) Appl. No.: 11/057,410

(22) Filed: Feb. 14, 2005

(65) Prior Publication Data
US 2006/0057114 A1 Mar. 16, 2006

Related U.S. Application Data

(63) Continuation of application No. PCT/US03/25508, filed on Aug. 13, 2003.

(60) Provisional application No. 60/403,108, filed on Aug. 13, 2002, provisional application No. 60/403,586, filed on Aug. 14, 2002.

(51) Int. Cl.
A01N 43/04 (2006.01)
A61K 31/70 (2006.01)
A01N 63/00 (2006.01)
A01N 65/00 (2006.01)
A61K 48/00 (2006.01)

(52) U.S. Cl. ................. 514/44; 424/93.1; 424/93.21

(58) Field of Classification Search .............. None
See application file for complete search history.

(56) References Cited

U.S. PATENT DOCUMENTS

| | | | |
|---|---|---|---|
| 5,798,366 A | 8/1998 | Platt et al. | |
| 5,910,488 A | 6/1999 | Nabel et al. | |
| 5,911,983 A | 6/1999 | Barranger et al. | |
| 5,994,136 A | 11/1999 | Naldini et al. | |
| 6,165,782 A | 12/2000 | Naldini et al. | |
| 6,218,181 B1 | 4/2001 | Verma et al. | |
| 6,730,297 B1 | 5/2004 | Davidson et al. | |
| 7,090,836 B2 * | 8/2006 | Desmaris et al. | 424/93.1 |
| 2002/0095135 A1 | 7/2002 | Meeker et al. | |

OTHER PUBLICATIONS

Eck, et al. (1996) The Pharmacological Basis of Therapeutics, 9th Ed., pp. 77-101, published by McGraw-Hill, N.Y.*
Kaye, et al. (2002) Neurol. Clin. 20(3): 879-901.*
Hartung, et al. (2004) Molecular Therapy, 9(6): 866-75.*
Ponder, et al. (2002) Proceedings of the National Academy of Science, USA, 99(20): 13102-07.*
Schauber (2004) Gene Therapy, 11: 266-75.*
Kobayashi, et al. (2005) Molecular Therapy, 11(5): 776-89.*
Blomer, Ulrike, "Highly efficient and sustained gene transfer in adult neurons with a lentivirus vector", Journal of Virology. 71(9), (Sep. 1997),6641-6649.

Di Natale, P. , et al., "In vitro Gene Therapy of Mucopolysaccharidosis Type I by Lentiviral Vectors", Eur. J. Biochem., 269, (2002),2764-2771.
Eto, Y. , et al., "Novel Treatment for Neuronopathic Lysosomal Storage Diseases-Cell Therapy / Gene Therapy", Current Molecular Medicine, 2, (Feb. 2002),83-89.
Johnson, et al., "Pseudotyped human lentiviral vector-mediated gene transfer to airway epithelia in vivo", Gene Therapy, 7, (2000),568-574.
Kafri, et al., "Sustained expression of genes delivered directly into liver and muscle by lentiviral vectors", Nat. Genet., 17(3), (Nov. 1997),314-317.
Larson, Beth, et al., "Evaluation of second and third generation lentiviral vector systemes fo rintegration and expression of alpha-L-Iduronidase in mucopolysaccharidosis type I", Cited in Molucular Therapy, 5(5), abstract 549,(May), 181, (2002).
Miyoshi, Hiroyuki , et al., "Transduction of Human CD34+ Cells That Mediate Long-Term Engraftment of NOD/SCID Mice by HIV Vectors", Science, 283, (1999),682-686.
Pan, Dao , et al., "Biodistribution and toxicity studies of VSVG-pseudotyped lentiviral vector after intravenous administration in mice with the observation of in vivo transduction of bone marrow", Molecular Therapy, 6(1), (Jul. 2002),19-29.
Pan, D , et al., "In Vivo transduction of murine mucopolysaccharidosis type I with a third-generation lentiviral vector system", Published in Molecular Therapy, 5(5), Abstract # 1060, Gene Therapy Center, Department of Pediatrics, Institute of Human Genetics, Univesity of Minnesota, Minneapolis,(2002),S344.
Park, F , et al., "Efficient lentiviral transduction of liver requires cell cycling in vivo", Nature Genetics, 24, (2000),49-52.
Villani, G. R., et al., "Correction of Mucopolysaccharldosis Type IIIb Fibroblasts by Lentiviral Vector-Mediated Gene Transfer", Biochem. J. 364, (2002),747-753.
Whitley, C. B., et al., "Bone marrow transplantation for Hurler syndrome: assessment of metabolic correction", Birth Defects Orig Artic Ser., 22(1), (1986),7-24.
Wolfe, John H., et al., "Gene transfer of low levels of B-glucoronidase corrects hepatic lysomal storage in a large animal model of mucopolysaccharidosis VII", Molecular Therapy, 2(6), (Dec. 2000), 552-61.
Xu, L , et al., "Transduction of hepatocytes after neonatal delivery of a Moloney murine leukemia virus based retroviral vector results in long-term expression of beta-glucuronidase in mucopolysaccharidosis VII dogs", Molecular Therapy, 5(2), (Feb. 2002),141-53.
Pan, D. , et al., "Retroviral Vector Design Studies Toward Hematopoietic Stem Cell Gene Therapy for Mucopolysaccharidosis Type I", Gene Therapy, 7, (2000),1875-1883.

* cited by examiner

Primary Examiner—Robert M Kelly
(74) Attorney, Agent, or Firm—Schwegman, Lundberg & Woessner, P.A.

(57) ABSTRACT

Isolated nucleic acid-based vectors and lentivirus vectors, and methods of using those vectors to inhibit or prevent metabolic disorders in a mammal, are provided.

10 Claims, 7 Drawing Sheets
(2 of 7 Drawing Sheet(s) Filed in Color)

TREATED, MPS I MOUSE CEREBELLUM 67 (−/−TREATED)

NORMAL MOUSE CEREBELLUM 11 (+/+)

UNTREATED, MPS I MOUSE CEREBELLUM 25 (−/−)

PLASMID pT-CAGGS-GUSB

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ccgacaagca gaagaacggc atca                                            24

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
ccttgagcag tgcccgacca ttc                                             23

<210> SEQ ID NO 3
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 3
actacaacag ccacaacgtc tatatca                                         27

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ggcggatctt gaagttcacc                                                 20

<210> SEQ ID NO 5
<211> LENGTH: 19
<212> TYPE: DNA
<213> ORGANISM: Artificial Sequence
```

-continued

```
<220> FEATURE:
<223> OTHER INFORMATION: Synthetic oligonucleotide

<400> SEQUENCE: 5
cgtgggctcc agcattcta                                                  19

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
tcaccagtca tttctgcctt tg                                              22
```

METHODS OF TREATING LYSOSOMAL STORAGE RELATED DISEASES BY GENE THERAPY

This application is a continuation under 35 U.S.C. 111(a) of PCT US/2003/025508, filed Aug. 13, 2003 and published on Jul. 1, 2004 as WO 2004/055 157 A2, which claims the benefit under 35 U.S.C. 119(e) of U.S. Provisional Application Ser. No. 60/403,108, filed on Aug. 13, 2002 and U.S. Provisional Application Ser. No. 60/403,586, filed Aug. 14, 2002, which are incorporated herein by reference.

STATEMENT OF GOVERNMENT RIGHTS

The invention was made at least in part with a grant from the Government of the United States of America (grant POI-HD32652 from the National Institutes Health). The Government may have certain rights to the invention.

BACKGROUND OF THE INVENTION

Many human genetic diseases are due to the deficiency of an enzyme or other protein. For example, the genetically determined deficiency of the lysosomal enzyme alpha-L-iduronidase results in the progressive accumulation of glycosaminoglycan substrates. In vitro evidence that cells grown in culture can take up exogenously supplied enzymes from the surrounding tissue culture medium led to the concept of in vivo enzyme replacement. For instance, enzyme replacement by intravenous infusion has been demonstrated to be successful for adenosine deaminase deficiency and for Gaucher disease, and some measures of efficacy have been found in human patients receiving weekly infusions of recombinant human alpha-L-iduronidase. However, these infusions must occur over a period of hours every week, and it is unclear if weekly administration of the enzyme would be efficacious, even if treatments are started early in life. Moreover, it is likely that enzyme infusions will not prevent progressive mental retardation associated with particular protein deficiencies.

Enzyme replacement may also be accomplished by transplantation of genetically normal cells and tissues, e.g., via bone marrow transplantation for mucopolysaccharidosis (also known as Hurler syndrome). For example, bone marrow transplantation was found to reduce many of the consequences of mucopolysaccharidosis type I and may prevent progression of mental retardation (Whitley et al., 1986). However, transplantation procedures which include the use of immunosuppressive medications are associated with an increase in morbidity and mortality.

Enzyme replacement may also be accomplished via gene therapy e.g., with viral vectors such as HIV-based vectors, ex vivo or in vivo. Lentiviral vectors are one type of viral vector which has been proposed as useful for mammalian gene therapy. HIV-based lentiviral vectors pseudotyped with the envelope of another virus (most often the G protein of the vesicular stomatitis virus, VSVG) have become promising tools for gene delivery into nondividing cells. These vectors have been shown to be capable of transferring genes into a range of nonproliferative cell types, including neurons, retinal cells, muscle cells, and hematopoietic pluripotent cells (Amado et al., 1999; Lever, 2000; Podsakoff, 2001) and, using local administration of those vectors, in vivo gene delivery has been accomplished in rat brain (Naldini et al., 1996; Blomer et al., 1997), liver and muscle (Kafri et al., 1997), retina (Miyoshi et al., 1999), and airway epithelia (Johnson et al., 2000).

However, the biosafety concerns surrounding HIV vectors have received considerable attention because of the pathogenic nature of HIV. Thus, efforts have been made to increase the safety of lentivirus vectors by minimizing the potential formation of replication-competent virus (RCR) via homologous recombination events. One strategy to reduce RCR formation has been to use nonoverlapping split-genome packaging constructs that require multiple recombination events with the transfer vector for RCR generation (Naldini et al., 1996; Reiser et al., 1996). Other strategies have focused on eliminating all unnecessary HIV reading frames from the system (Kim et al., 1998; Dull et al., 1998) or truncating the 3' long terminal repeat (3' LTR) to generate self-inactivating HIV vectors (Miyoshi et al., 1998).

Lentiviral vectors have been a preferred vector for ex vivo modification of hematopoietic (i.e., blood-forming) stem cells as lentiviral vectors are likely capable of transducing such nondividing types of cells. Nevertheless, despite thousands of experiments attempting ex vivo gene transfer into hematopoietic stem cells, this vector-cell combination has not been successful in animal models of disease. Moreover, there has never been a successful clinical response in an animal using in vivo lentiviral gene therapy, probably owing to insufficient delivery of vector, or lack of expression of therapeutic protein, to the disease-causing tissues or cells.

Thus, what is needed is an improved method to prevent, inhibit or treat metabolic disorders characterized by a lack of, or a reduction in the amount of, an enzyme in a mammal.

SUMMARY OF THE INVENTION

The invention provides a lentivirus vector comprising a nucleic acid segment encoding a gene product such as a protein, the absence or reduced levels of which are associated with a disorder in a mammal, a disorder including, but not limited to, a metabolic disorder, e.g., a lysosomal storage disease, hemophilia, or adrenoleukodystrophy. A lentivirus includes ovine, caprine, equine, bovine and primate, e.g., HIV-1, HIV-2 and SIV, lentiviruses. Also provided is a method in which a recombinant lentivirus comprising a nucleic acid segment encoding a gene product, the absence or reduced levels of which in a mammal are associated with a disorder, is administered to a mammal having or at risk of having such a disorder, in an amount effective to prevent, inhibit or treat at least one symptom associated with the disorder, e.g., a neurological symptom. In one embodiment, the recombinant virus is administered into a vascular compartment, e.g., intravenously, of the mammal. Preferred amounts of virus include, but are not limited to, $1 \times 10^3$ to $1 \times 10^{15}$ TU, e.g., $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$ or $1 \times 10^{15}$ TU, although other amounts may be efficacious. Preferably, the mammal is a neonate or juvenile, although it is envisioned that adult mammals, and the developing embryo or fetus in utero, may also be treated.

In one embodiment, the recombinant lentivirus encodes a lysosomal enzyme and is administered in an amount which is effective to prevent, inhibit or treat a lysosomal storage disease in a mammal. Lysosomal storage diseases include, but are not limited to, mucopolysaccharidosis diseases, for instance, mucopolysaccharidosis type I, e.g., Hurler syndrome and the variants Scheie syndrome and Hurler-Scheie syndrome (a deficiency in alpha-L-iduronidase); Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV e.g., mucopolysaccharidosis type IV, e.g., Morquio syndrome (a deficiency of galactosamine-6-sulfate sulfatase or beta-galactosidase); mucopolysaccharidosis type VI. e.g., Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexosaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of a npc1 gene encoding a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol ester hydrolase); Deoxyribonuclease I-like 1 disorder, arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria. In particular, the invention is useful to prevent, inhibit or treat lysosomal storage diseases wherein the lysosomal enzyme is trafficked to the lysosome (within the cell and between cells) by specific glycosylation. For most lysosomal enzymes and their corresponding diseases, this would be by means of a terminal mannose-6-phosphate, however, it also includes terminal mannose glycosylation, e.g., in the case of beta-glucocerebrosidase deficiency responsible for Gaucher disease. Thus, in one embodiment, the lentivirus vector of the invention is useful to prevent, inhibit or treat lysosomal storage diseases including but are not limited to, mucopolysaccharidosis diseases, for instance, mucopolysaccharidosis type I, e.g., Hurler syndrome and the variants Scheie syndrome and Hurler-Scheie syndrome (a deficiency in alpha-L-iduronidase); mucopolysaccharidosis type II, e.g., Hunter syndrome (a deficiency of iduronate-2-sulfatase); mucopolysaccharidosis type III, e.g., Sanfilippo syndrome (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV, e., Morquio syndrome (a deficiency of galactosamine-6-sulfate sulfatase or beta-galactosidase); mucopolysaccharidosis type VI, e.g., Maroteaux-Lamy syndrome (deficiency of arylsulfatase B); mucopolysaccharidosis type VII, e.g., Sly syndrome (a deficiency in beta-glucuronidase); Tay-Sachs disease (a deficiency in alpha subunit of beta-hexosaminidase); Sandhoff disease (a deficiency in both alpha and beta subunit of beta-hexosaminidase); GM1 gangliosidosis; Fabry disease (a deficiency in alpha-galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase). As described herein, a single administration of a lentivirus encoding alpha-L-iduronidase to newborn Hurler syndrome mice resulted in normal patterns of behavior for the treated mice relative to untreated mice. Administration of the lentivirus to newborns likely resulted in an increased efficiency of transduction which may in turn be due to the presence of cells that are more susceptible to infection in the newborn. Early therapy, e.g., prenatal or in newborns, for metabolic disorders such as lysosomal storage diseases may thus be particularly efficacious.

In one embodiment, a recombinant lentivirus encoding a lysosomal enzyme is administered to a mammal in an amount which is effective to increase the level and/or activity of one or more lysosomal storage proteins, e.g., enzymes, and/or decrease skeletal deformity including kyphoscoliosis, scoliosis, deformity or arthritis of the hip joints, contractures of the digits or larger joints at the knees, ankles, elbows and shoulders, disfigurement of the face, recurrent and chronic ear infections, enlargement, dysfunction of an organ such as the liver, spleen or heart, obstuction of the coronary arteries causing myocardial infarction, respiratory abnormality such as obstructive airway disease, reactive airway disease or pneumonia, brain or other nervous system damage, and/or dysfunction such as hydrocephalus, cranial nerve compression, hearing loss, blindness, spinal cord compression.

In one embodiment, a recombinant lentivirus encoding a lysosomal enzyme is administered to a mammal in an amount which is effective to increase longevity, preserve intellect, e.g., measured by intelligence quotient (IQ), reduce ear infections, reduce skeletal deformity with improved ambulation, e.g., measured in a 6-minute walk test or other measurements of endurance, reduce organ size (e.g., liver, spleen), improve respiratory function, e.g., measured by improved by spirometry, normalize of organ cellular architecture, e.g., observed by decreased pathology (reduced lysosomal vacuolization or other microscopic pathology), decrease occlusion of the coronary arteries, reduce aberrant thickening of the meninges of the central nervous system, prevent or reduce hydrocephalus of the brain, decrease levels of pathologic substrates such as decreased glycosaminoglycan in the liver and other tissues, urine, or cerebrospinal fluid, and/or increase levels of a deficient enzyme such as alpha-L-iduronidase in liver tissue, white blood cells or plasma.

In one embodiment, a recombinant lentivirus encoding a lysosomal enzyme is administered intravenously to a mammal, e.g., a fetus (prenatal delivery), an infant (e.g., a human from birth to 2 years of age), a child (e.g., a human from over 2 years to 12 years or age), a juvenile (e.g., a human from over 12 years to 18 years of age), or an adult (e.g., a human older than 18 years of age).

In another embodiment, the invention provides a lentivirus vector comprising a nucleic acid sequence encoding a clotting factor, e.g., Factor VIII or Factor IX, and a method to prevent, inhibit or treat a mammal having or at risk of having the clotting disorder which employs a recombinant lentivirus comprising the vector. Preferably, the recombinant lentivirus is administered to a vascular compartment of the mammal.

Further provided is a lentivirus vector comprising a nucleic acid sequence encoding an ABC protein such as a peroxisomal transport protein, e.g., the X-ALD protein (ALDP), the adrenoleukodystrophy-related protein (ALDRP), the 70 kDa peroxisomal membrane protein (PMP70), or a PMP70-related protein, and a method to prevent, inhibit or treat a mammal having or at risk of an adrenoleukodystrophy which employs a recombinant lentivirus comprising the vector. Preferably, the lentivirus is administered to a vascular compartment of the mammal.

The invention also provides a recombinant lentivirus of the invention, a host cell transfected with a lentivirus vector of the invention, e.g., eukaryotic host cells including mammalian host cells such as human, non-human primate, canine, caprine, feline, bovine, equine, swine, ovine, rabbit or rodent cells, a host cell infected, e.g., ex vivo, with a recombinant lentivirus of the invention, and a method of expressing a biologically active protein in a cell which employs a lentivirus vector or lentivirus of the invention which encodes the biologically active protein. A "biologically active" protein is a protein which has substantially the same activity, e.g., at least 80%, more preferably at least 90%, the activity of a corresponding wild-type (functional) protein.

Also provided is a kit comprising a recombinant lentivirus of the invention, e.g., a lyophilized or frozen preparation of recombinant lentivirus.

Mucopolysaccharidosis (MPS) type VII is an autosomal recessive lysosomal storage disease resulting from deficiency of beta-glucuronidase due to mutations of the corresponding gene for beta-glucuronidase, GUSB. As described herein, a plasmid was constructed to express the human GUSB cDNA under the transcriptional regulation of a hybrid promoter-enhancer (CAGGS) containing the chicken beta-actin enhancer and CMV early promoter. Sleeping Beauty transposon IR sequences were included to examine the potential for integration into the cell chromosome. This transposed plasmid pT-CAGGS-GUSB was administered by hydrodynamic injection (i.e., intravenous infusion in a volume equal to 10% of body weight, over about 8-10 seconds) into the tail vein of mice ranging from 4 to 23 weeks of age. The pT-CAGGS-GUSB plasmid was administered (25 mcg/animal) alone (Group 1), or with transposase plasmid pSBI0, at a transposon:transposase molar ratio of 1:1 (Group 2), or 10:1 (Group 3). Forty-eight hours after injection, plasma beta-glucuronidase enzymatic activity in treated MPS mice was markedly elevated (1,552-7,711 mmol/ml/hr, n=14) in comparison to that of wild-type, untreated or sham-treated mice (9-15 nmol/ml/hr, n=6). In liver, beta-glucuronidase activity in treated MPS mice was also markedly elevated (1,860-6,185 nmol/mg/hr, n=4) compared to normal levels (86-188 nmol/mg/hr). Notably, the liver tissue of MPS mice receiving pTCAGGS-GUSB stained uniformly positive for beta-glucuronidase activity, including both Kupffer cells and hepatocytes. One week after injection, plasma beta-glucuronidase activity was reduced relative to day 2 levels: Group 1, 59-93% of the 2-day levels; Group 2, 21-36%; and Group 3, 33-63% (n=4 in each group). Beta-glucuronidase levels in the liver and spleen were 184-185 nmol/mg/hr and 4,534-6,080, respectively, while levels in other organs were lower (heart 94-98, lung 49-65, kidney 59, and undetectable in the brain). Two months after injection, beta-glucuronidase activity remained at therapeutic levels in animals receiving pT-CAGGS-GUSB plasmid alone. Histochemical studies showed staining for beta-glucuronidase activity throughout the liver and spleen. Remarkably, mice co-injected with pSBIO had much lower levels of beta-glucuronidase activity. Morphometric analysis of inclusion morphology demonstrated that clearing of hepatic lysosomal pathology was related to the level of beta-glucuronidase, and that mice receiving pT-CAGGS-GUSB plasmid alone were completely clear of pathology.

Thus, hydrodynamic infusion of the pT-CAGGS-GUSB transposon delivered DNA to liver with marked increase in enzyme activity, with the highest levels in blood ever achieved. GUSB enzymatic activity was d throughout the liver transiently reaching levels 10- to 1,000-fold of normal levels, levels which are above those that would be curative in newborns.

The results described herein with the lentivirus and plasmid vectors of the invention were surprising as the intravenous administration of other vectors did not show the extent of correction observed with the lentivirus and plasmid vectors. Moreover, PCR analysis of gonads, e.g., testes, showed virtually no evidence of viral vector sequences, indicating a decreased risk for germ line transmission. Further, viral vector sequences were surprisingly detected in bone marrow stem cells after intravenous administration of a lentivirus vector of the invention to a mammal and so those vectors are particularly useful for systemic expression of therapeutic genes.

The invention provides a method to prevent, inhibit or treat a metabolic disorder in a mammal via the hydrodynamic infusion of a plasmid encoding a gene product, the expression of which in the mammal prevents, inhibits, or treats one or more symptoms of the disorder. In one embodiment, a fetus or neonate is infused via the umbilical cord with a vector of the invention.

The invention provides a method to prevent, inhibit or treat a metabolic disorder such as one characterized by the absence or reduced levels of a lysosomal protein in a mammal. The method comprises administering to a mammal, e.g., to a vascular compartment of a mammal having or at risk of the disorder an effective amount of an isolated nucleic acid molecule comprising a nucleic acid sequence encoding the protein, e.g., a biologically active protein. In one embodiment, the nucleic acid molecule comprises a promoter operably linked to the nucleic acid sequence.

The invention also provides isolated nucleic acid-based vectors to inhibit or treat metabolic disorders, e.g., lysosomal storage disease such as mucopolysaccharidosis type I diseases, e.g., Hurler syndrome, mucopolysaccharidosis type II diseases, e.g., Hunter syndrome, mucopolysaccharidosis type II diseases, e.g., Sanfilippo syndrome, mucopolysaccharidoses type VII diseases, e.g., Sly disease, Fabry disease, Gaucher disease as well as hemophilia, e.g., Factor VIII or factor IX deficiency. Further provided is a method to prevent, inhibit or treat a metabolic disorder in a mammal which employs an isolated nucleic acid vector of the invention, e.g., in an amount effective to prevent, inhibit or treat at least one symptom associated with the disorder, e.g., a neurological symptom associated with the disorder. In one embodiment, the mammal is an adult. In one embodiment, the isolated nucleic acid vector of the invention is administered two or more times to the mammal.

In another embodiment, the invention provides an isolated nucleic acid molecule comprising a nucleic acid sequence encoding a clotting factor, e.g., Factor VM or Factor IX, and a method to prevent, inhibit or treat a mammal having or at risk of having the clotting disorder which employs a vector comprising the nucleic acid molecule. Preferably, the vector is administered to a vascular compartment of the mammal.

Further provided is an isolated nucleic acid molecule comprising a nucleic acid sequence encoding an ABC protein such as a peroxisomal transport protein, e.g., the X-ALD protein (ALDP), the adrenoleukodystrophy-related protein (ALDRP), the 70 kDa peroxisomal membrane protein (PMP70), or a PMP70-related protein, and a method to prevent, inhibit or treat a mammal having or at risk of an adrenoleukodystrophy which employs a vector comprising the nucleic acid molecule. Preferably, the lentivirus is administered to a vascular compartment of the mammal.

The invention also provides an isolated nucleic acid molecule of the invention, a host cell transfected with the isolated nucleic acid molecule of the invention, e.g., eukaryotic host cells including mammalian host cells such as human, non-human primate, canine, caprine, feline, bovine, equine, swine, ovine, rabbit or rodent cells, a host cell transfected, e.g., ex vivo, with an isolated nucleic acid molecule of the invention, and a method of expressing a biologically active protein in a cell which employs a vector comprising a nucleic acid molecule of the invention which encodes the biologically active protein.

BRIEF DESCRIPTION OF THE FIGURES

The patent or application file contains at least one drawing executed in color. Copes of this patent or patent application publication with color drawings will be provided by the Office upon request and payment of the necessary fee.

DETAILED DESCRIPTION OF THE INVENTION

Definitions

Figure 1:
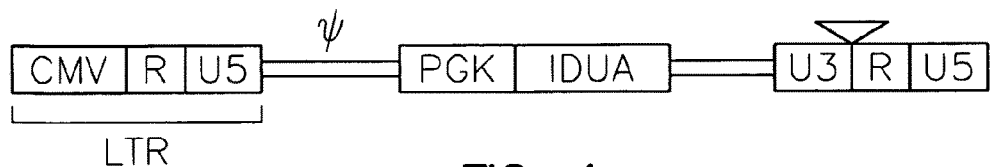
FIG. 1 shows the genetic map of a representative lentiviral vector for intravascular administration. LTR is the "long terminal repeat" of HIV-1 virus; $\psi^+$ is the packing signal; CMV refers to a promoter from cytomegalovirus that regulates gene expression; PGK refers to a phosphoglyerate kinase promoter; the inverted triangle indicates a modification which results in a "self inactivating" vector; and IDUA refers to a cDNA sequence encoding the therapeutic protein alpha-L-iduronidase.

"Inducible expression system" includes a construct or combination of constructs that includes a nucleotide sequence encoding a transactivator, an inducible promoter that can be transcriptionally activated by the transactivator, and a nucleotide sequence of interest operably linked to the inducible promoter. For example, an exemplary inducible expression system of the invention includes a nucleotide sequence encoding a tetracycline operon regulatable transactivator (tTA) and a nucleotide sequence of interest operably linked to an inducible promoter composed of a minimal promoter operably linked to at least one tetO sequence.

"Transactivator," "transactivating factor," or "transcriptional activator" includes a polypeptide that facilitates transcription from a promoter. Where the promoter is an inducible promoter, the transactivator activates transcription in response to a specific transcriptional signal or set of transcriptional signals. For example, in the inducible expression system of the invention, tTA is a transactivator that facilitates transcription from the inducible tetO promoter when tTA is not bound to tetracycline.

"Tetracycline repressor protein," "tetracycline repressor polypeptide," "tetR polypeptide," and "tetR protein" are used interchangeably herein to include a polypeptide that exhibits both 1) specific binding to tetracycline and/or tetracycline derivatives; and 2) specific binding to tetO sequences when the tetR polypeptide is not bound by tetracycline or a tetracycline analog(s). "TetR polypeptide" is meant to include a naturally occurring (i.e., native) tetR polypeptide sequence and functional derivatives thereof "Transcriptional activation domain" includes a polypeptide sequence that facilitates transcriptional activation from a promoter. "Transcriptional activation domain" includes transcriptional activation domains derived from the naturally occurring amino acid sequence of a transcription factor as well as functional derivatives thereof.

"Envelope protein" includes a polypeptide that 1) can be incorporated into an envelope of a retrovirus; and 2) can bind target cells and facilitate infection of the target cell by the RNA virus that it envelops. "Envelope protein" is meant to include naturally occurring (i.e., native) envelope proteins and functional derivatives thereof that 1) can form pseudotyped retroviral virions according to the invention, and 2) exhibit a desired functional characteristic(s) (e.g., facilitate viral infection of a desired target cell, and/or exhibit a different or additional biological activity). In general, envelope proteins of interest in the invention include any viral envelope protein that can, in combination with a retroviral genome, retroviral Pol, retroviral Gag, and other essential retroviral components, form a retroviral particle. Such envelope proteins include retroviral envelope proteins derived from any suitable retrovirus (e.g., an amphotropic, xenotropic, ecotropic or polytropic retrovirus) as well as non-retroviral envelope proteins that can form pseudotype retroviral virions (e.g., VSV G). Envelope proteins of particular interest include, but are not limited to, envelope protein of vesicular stomatitis virus (VSV G), HTLV-1, gibbon ape leukemia virus (GALV), Sindai virus, influenza virus, herpes virus, rhabdovirus, and rabies virus.

"Functional derivative of a polypeptide" includes an amino acid sequence derived from a naturally occurring polypeptide that is altered relative to the naturally occurring polypeptide by virtue of addition, deletion, substitution, or other modification of the amino acid sequence. "Functional derivatives" contemplated herein exhibit the characteristics of the naturally occurring polypeptide essential to the operation of the invention. For example, by "functional derivative of tetR" is meant a polypeptide derived from tetR that retains both 1) tetracycline or tetracycline analog binding and 2) the ability to inhibit transcriptional activation by tTA when bound to tetracycline or an analog thereof.

"Promoter" includes a minimal DNA sequence sufficient to direct transcription of a DNA sequence to which it is operably linked. The term "promoter" is also meant to encompass those promoter elements sufficient for promoter-dependent gene expression controllable for cell-type specific expression, tissue-specific expression, or inducible by external signals or agents; such elements may be located in the 5' or 3' regions of the naturally occurring gene.

"Inducible promoter" includes a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/r affect function of the transcriptional activator itself. For example, the transcriptional activator of the present invention, tTA, induces transcription from its corresponding inducible promoter when tetracycline is absent, i.e., tetracycline is not bound to tTA.

"Construct" includes a recombinant nucleotide sequence, generally a recombinant DNA molecule, that has been generated for the purpose of the expression of a specific nucleotide sequence(s), or is to be used in the construction of other recombinant nucleotide sequences. In general, "construct" is used herein to refer to a recombinant DNA molecule.

"Operably linked" includes a DNA sequence and a regulatory sequence(s) are connected in such a way as to permit gene expression when the appropriate molecules (e.g., transcriptional activator proteins) are bound to the regulatory sequence(s).

"Isolated" when used in relation to a nucleic acid, as in "isolated oligonucleotide" or "isolated polynucleotide" includes a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may single-stranded), but may contain both the sense and anti-sense strands (i.e., the oligonucleotide may be double-stranded). In one embodiment, the isolated nucleic acid is one which is free of viral proteins, i.e., it is not a viral particle, and/or does not encode one or more viral proteins.

"Operatively inserted" refers to a nucleotide sequence of interest is positioned adjacent a nucleotide sequence that directs transcription and translation of the introduced nucleotide sequence of interest (i.e., facilitates the production of, e.g., a polypeptide encoded by a DNA of interest).

By "packaging cell line" is meant a line of packaging cells selected for their ability to package defective retroviral vectors at a titer of generally greater than $10^3$ virions per milliliter of tissue culture medium, having less than 10 helper virus virions per milliliter of tissue culture medium, and capable of being passaged in tissue culture without losing their ability to package defective retroviral vectors.

"Transformation" includes a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

"Target cell" is a cell(s) that is to be transformed using the methods and compositions of the invention. Transformation may be designed to non-selectively or selectively transform the target cell(s). In general, target cell as used herein means a eukaryotic cell that can be infected by a VSV G pseudotyped retroviral vector according to the invention.

"Transformed cell" is a cell into which (or into an ancestor of which) has been introduced, by means of recombinant DNA techniques, a DNA molecule encoding a gene product (e.g., RNA and/or protein) of interest (i.e., nucleic acid encoding a therapeutic cellular product).

"Nucleotide sequence of interest", "gene of interest" or "DNA of interest" includes any nucleotide or DNA sequence that encodes a protein or other molecule that is desirable for expression in a host cell (e.g., for production of the protein or other biological molecule (e.g., a therapeutic cellular product) in the target cell). The nucleotide sequence of interest is generally operatively linked to other sequences which are needed for its expression, e.g., a promoter. In general, a nucleotide sequence of interest present in the genome of a recombinant retroviral particle of the invention encodes any gene product of interest, usually a therapeutic gene product where the recombinant retroviral particle is to be used to transform cells in in vivo (e.g., in a gene therapy application in humans).

A "therapeutic gene product" includes a polypeptide, RNA molecule or other gene product that, when expressed in a target cell, provides a desired therapeutic effect, e.g., repair of a genetic defect in the target cell genome (e.g., by complementation), expression of a polypeptide having a desired biological activity, and/or expression of an RNA molecule for antisense therapy (e.g., regulation of expression of a endogenous or heterologous gene in the target cell genome).

By "subject" or "patient" is meant any subject for which cell transformation or gene therapy is desired, including humans, cattle, dogs, cats, guinea pigs, rabbits, mice, insects, horses, chickens, and any other genus or species having cells that can be infected with a viral vector having an envelope containing VSV G or other envelope described herein.

A "transgenic organism" includes a non-human organism (e.g., single-cell organisms (e.g., yeast), mammal, non-mammal (e.g., nematode or *Drosophila*)) having a non-endogenous (i.e., heterologous) nucleic acid sequence present as an extrachromosomal element in a portion f its cells or stably integrated into its germ line DNA.

A "transgenic animal" includes a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its heterologous nucleic acid is introduced into the germ line of such transgenic animals by genetic manipulation of, for example, embryos or embryonic stem cells of the host animal.

A "viral vector" includes a recombinant viral particle that accomplishes transformation of a target cell with a nucleotide sequence of interest.

A "virion," "viral particle," or "retroviral particle" includes a single virus minimally composed of an RNA genome, a viral polymerase, e.g., a Pol protein (for reverse transcription of the RNA genome following infection), a viral glycoprotein Gag protein (structural protein present in the nucleocapsid), and an envelope protein. As used herein, the RNA genome of a retroviral or lentiviral particle is usually a recombinant RNA genome, e.g., contains an RNA sequence exogenous to the native retroviral genome and/or is defective in an endogenous retroviral lentiviral sequence (e.g., is defective in pol, gag, and/or env, and, as used herein, is normally defective in all three genes).

"Pseudotyped viral particle," or "pseudotyped retroviral particle" includes a viral particle having an envelope protein that is from a virus other than the virus from which the RNA genome is derived. For instance, the envelope protein can be from a retrovirus of a species different from a retrovirus from which the RNA genome is derived or from a non-retroviral virus (e.g., vesicular stomatitis virus (VSV)). Preferably, the envelope protein of the pseudotyped retroviral particle is VSV G.

By "VSV G" or "VSV G envelope protein" is meant the envelope protein of vesicular stomatitis virus (VSV) or a polypeptide derived therefrom or recombinant fusion polypeptide having a VSV G polypeptide sequence fused to a heterologous polypeptide sequence, where the VSV G-derived polypeptide of recombinant fusion polypeptide can be contained in a viral envelope of a pseudotyped retroviral particle and retains infectivity for a desired target cell (e.g., a range of desired eukaryotic cells, or a specific target cell of interest).

By "VSV G pseudotyped virus," "VSV G pseudotyped retrovirus," "VSV G pseudotyped viral particle," or "VSV G pseudotyped retroviral particle," is meant a retrovirus having the envelope protein VSV G, e.g., either in combination with or substantially substituted for the endogenous retroviral envelope. Preferably, VSV G is present in the VSV G pseudotyped viral envelope such that VSV G represents about 50% of the envelope protein(s) present in the envelope, more preferably about 75%, even more preferably about 90% to about 95%, still more preferably greater than about 95%, most preferably about 100% or such that VSV G is substantially the only envelope protein present in the pseudotyped viral particle envelope.

Vectors for Recombinant Lentivirus Production

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3'LTR's serve to promote transcription and polyadenylation of the virion RNA's. The LTR contains all other cis-acting sequences necessary for viral replication. Lentiviruses have additional genes including vif vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

The invention provides a method of producing a recombinant lentivirus capable of infecting a cell, e.g., non-dividing cell, comprising transfecting a suitable host cell with two or more vectors carrying the packaging functions, namely gag, pol and env, as well as rev and tat. As will be disclosed hereinbelow, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the heterologous gene of interest.

Generally the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

According to the above-indicated configuration of vectors and heterologous genes, the second vector can provide a nucleic acid encoding a viral envelope (env) gene. The env gene can be derived from any virus, including retroviruses, e.g., lentiviruses, and heterologous viruses such as VSV. The env preferably is an envelope protein which allows transduction of cells of human and other species.

It may be desirable to target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector. Those of skill in the art will know of, or can readily ascertain without undue experimentation, specific methods to achieve delivery of a retroviral vector to a specific target.

Examples of retroviral-derived env genes include, but are not limited to: Moloney murine leukemia virus (MoMuLV or MMLV), Harvey murine sarcoma virus (HaMuSV or HSV), murine mammary tumor virus (4 uMTV or MMTV), gibbon ape leukemia virus (GaLV or GALV), human immunodeficiency virus (HIV), Rous sarcoma virus (RSV), and env genes of amphotropic viruses. Other env genes such as Vesicular stomatitis virus (VSV) protein G (VSV G), that of hepatitis viruses and of influenza also can be used.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus (CMV) enhancer or the vaccinia P7.5 promoter. In some cases, such as the Moloney murine leukemia virus promoter-enhancer element, the promoter-enhancer elements are located within or adjacent to the LTR sequences.

Preferably, the regulatory sequence is one which is not endogenous, i.e., it is heterologous, to the lentivirus from which the vector is being constructed. Thus, if the vector is being made from SIV, the SIV regulatory sequence found in the SIV LTR would be replaced by a regulatory element which does not originate from SIV.

While VSV G protein is a desirable env gene because VSV G confers broad host range on the recombinant virus, VSV G can be deleterious to the host cell. Thus, when a gene such as that for VSV G is used, it is preferred to employ an inducible promoter system so that VSV G expression can be regulated to minimize host toxicity when VSV G is expression is not required. For example, the tetracycline-regulatable gene expression system of Gosse et al. (1992) can be employed to provide for inducible expression of VSV G when tetracycline is withdrawn from the transfected cell. Thus, the tet/VP16 transactivator is present on a first vector and the VSV G coding sequence is cloned downstream from a promoter controlled by tet operator sequences on another vector.

The heterologous nucleic acid sequence of interest, the transgene, is linked operably to a regulatory nucleic acid sequence. As used herein, the term "heterologous" nucleic acid sequence refers to a sequence that originates from a foreign species, or, if from the same species, it may be substantially modified from the original form. Alternatively, an unchanged nucleic acid sequence that is not expressed normally in a cell is a heterologous nucleic acid sequence.

The term "operably linked" refers to functional linkage between a regulatory sequence and a heterologous nucleic acid sequence resulting in expression of the latter. Preferably, the heterologous sequence is linked to a promoter, resulting in a chimeric gene. The heterologous nucleic acid sequence is preferably under control of either the viral LTR promoter-enhancer signals or of an internal promoter, and retained signals within the retroviral LTR can still bring about efficient expression of the transgene.

The heterologous gene of interest can be any nucleic acid of interest which can be transcribed. Generally the foreign gene encodes a polypeptide. Preferably the polypeptide has some therapeutic benefit. The polypeptide may supplement deficient or nonexistent expression of an endogenous protein in a host cell. The polypeptide can confer new properties on the host cell, such as a chimeric signalling receptor, see U.S. Pat. No. 5,359,046. The artisan can determine the appropriateness of a heterologous gene practicing techniques taught herein and known in the art. For example, the artisan would know whether a heterologous gene is of a suitable size for encapsidation and whether the heterologous gene product is expressed properly.

The method of the invention may also be useful for neuronal, glial, fibroblast or mesenchymal cell transplantation, or "grafting", which involves transplantation of cells infected with the recombinant lentivirus of the invention ex vivo, or infection in vivo into the central nervous system or into the ventricular cavities or subdurally onto the surface of a host brain. Such methods for grafting will be known to those skilled in the art and are described in Neural Grafting in the Mammalian CNS, Bjorklund & Stenevi, eds. (1985).

For diseases due to deficiency of a protein product, gene transfer could introduce a normal gene into the affected tissues for replacement therapy, as well as to create animal models for the disease using antisense mutations. For example, it may be desirable to insert a Factor VIII or IX encoding nucleic acid into a lentivirus for infection of a muscle, spleen or liver cell.

The promoter sequence may be homologous or heterologous to the desired gene sequence. A wide range of promoters may be utilized, including a viral or a mammalian promoter. Cell or tissue specific promoters can be utilized to target expression of gene sequences in specific cell populations. Suitable mammalian and viral promoters for the instant invention are available in the art.

Optionally during the cloning stage, the nucleic acid construct referred to as the transfer vector, having the packaging signal and the heterologous cloning site, also contains a selectable marker gene. Marker genes are utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate etc. and cell surface markers.

The recombinant virus of the invention is capable of transferring a nucleic acid sequence into a mammalian cell. The term, "nucleic acid sequence", refers to any nucleic acid molecule, preferably DNA, as discussed in detail herein. The nucleic acid molecule may be derived from a variety of sources, including DNA, cDNA, synthetic DNA, RNA or combinations thereof. Such nucleic acid sequences may comprise genomic DNA which may or may not include naturally occurring introns. Moreover, such genomic DNA may be obtained in association with promoter regions, poly A sequences or other associated sequences. Genomic DNA may be extracted and purified from suitable cells by means well known in the art. Alternatively, messenger RNA (mRNA) can be isolated from cells and used to produce cDNA by reverse transcription or other means.

Preferably, the recombinant lentivirus produced by the method of the invention is a derivative of human immunodeficiency virus (HIV). The env will be derived from a virus other than HIV.

Thus, three or more vectors, e.g., in one or more plasmids, which provide all of the functions required for packaging of recombinant virions, such as, gag, pol, env, tat and rev, can be employed to prepare recombinant lentivirus. As noted herein, tat may be deleted. There is no limitation on the number of vectors which are utilized so long as the vectors are used to transform and to produce the packaging cell line to yield recombinant lentivirus.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art.

Thus, the packaging constructs can be introduced into human cell lines by calcium phosphate transfection, lipofection or electroporation, generally together with a dominant selectable marker encoding, for example, neomycin resistance, DHFR, Gln synthetase or ADA, followed by selection in the presence of the appropriate drug and isolation of clones. The selectable marker gene can be linked physically to the packaging genes in the construct.

Stable cell lines wherein the packaging functions are configured to be expressed by a suitable packaging cell are known. For example, see U.S. Pat. No. 5,686,279; and Ory et al. (1996), which describe packaging cells.

Zufferey et al. (1997) teach a lentiviral packaging plasmid wherein sequences 3' of pol including the HIV-1 env gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of env can be removed. Moreover, steps can be taken to modify the vector to enhance the splicing and translation of the RNA.

To provide a vector with an even more remote possibility of generating replication competent lentivirus, lentivirus packaging plasmids wherein tat sequences, a regulating protein which promotes viral expression through a transcriptional mechanism, are deleted functionally. Thus, the tat gene can be deleted, in part or in whole, or various point mutations or other mutations can be made to the tat sequence to render the gene non-functional. An artisan can practice known techniques to render the tat gene non-functional.

The techniques used to construct vectors, and to transfect and to infect cells, are practiced widely in the art. Practitioners are familiar with the standard resource materials which describe specific conditions and procedures.

A lentiviral packaging vector is made to contain a promoter and other optional or requisite regulatory sequences as determined by the artisan, gag, pol rev, env or a combination thereof, and with specific functional or actual excision of tat, and optionally other lentiviral accessory genes.

Lentiviral transfer vectors (Naldini et al., 1996) have been used to infect human cells growth-arrested in vitro and to transduce neurons after direct injection into the brain of adult rats. The vector was efficient at transferring marker genes in vivo into the neurons and long term expression in the absence of detectable pathology was achieved. Another version of the lentiviral vector in which the HIV virulence genes env, vif, vpr; vpu and nef were deleted without compromising the ability of the vector to transduce non-dividing cells, represents a substantial improvement in the biosafety of the vector (Zufferey et al., 1997).

In transduced cells, the integrated lentiviral vector generally has an LTR at each termini. The 5' LTR may cause accumulation of "viral" transcripts that may be the substrate of recombination, in particular in HIV-infected-cells. The 3' LTR may promote downstream transcription with the consequent risk of activating a cellular protooncogene. The U3 sequences comprise the majority of the HIV LTR. The U3 region contains the enhancer and promoter elements that modulate basal and induced expression of the HIV genome in infected cells and in response to cell activation. Several of the promoter elements are essential for viral replication. Some of the enhancer elements are highly conserved among viral isolates and have been implicated as critical virulence factors in viral pathogenesis. The enhancer elements may act to influence replication rates in the different cellular target of the virus (Marthas et al., 1993). Also, enhancers in either LTR can activate transcription of neighboring genes.

As viral transcription starts at the 3' end of the U3 region of the 5' LTR, this U3 region (including the promoter and enhancer) is not included in the viral mRNA, and a copy thereof from the 3' LTR acts as template for the generation of the U3 region of both LTR's in the subsequently integrated provirus. If the U3 region of the 3' LTR is altered in a retroviral vector construct so as to eliminate the promoter and enhancer, the vector RNA still is produced from the intact 5' LTR in producer cells, but cannot be regenerated in target cells. Transduction of such a vector results in the transcriptional inactivation of both LTR's in the progeny virus. Thus, the retrovirus is self-inactivating (SIN) and those vectors are known as Sin transfer vectors.

There are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3' LTR may decrease polyadenylation of vector transcripts with adverse consequences both on the titer of the vector in producer cells and the transgene expression in target cells. On the other hand, limited deletions may not abrogate the transcriptional activity of the LTR in transduced cells.

U3 deletions in a HIV LTR can span from nucleotide −418 of the U3 LTR to the indicated position: SIN-78, SIN-45, SIN-36 and SIN-18. Lentiviral vectors with almost complete deletion of the U3 sequences from the 3' LTR were developed without compromising either the titer of vector in producer cells or transgene expression in target cells. The most extensive deletion (−418 to −18) extends as far as to the TATA box, therefore abrogating any transcriptional activity of the LTR in transduced cells. Thus, the lower limit of the 3' deletion may extend as far as including the TATA box. The deletion may be of the remainder of the U3 region up to the R region. Surprisingly, the average expression level of the transgene is higher in cells transduced by the SIN vectors as compared to more intact vectors.

The 5' LTR of a transfer vector construct can be modified by substituting part or all of the transcriptional regulatory elements of the U3 region with heterologous enhancer/promoters. The changes were made to enhance the expression of transfer vector RNA in producer cells; to allow vector production in the absence of the HIV tat gene; and to remove the upstream wild-type copy of the HIV LTR that can recombine with the 3' deleted version to "rescue" the above described SIN vectors.

Thus, vectors containing the above-described alterations at the 5' LTR, 5' vectors, can find use as transfer vectors because of the sequences to enhance expression and in combination with packaging cells that do not express tat. Such 5' vectors can also carry modifications at the 3' LTR as discussed hereinabove to yield improved transfer vectors which have not only enhanced expression and can be used in packaging cells that do not express tat but can be self-inactivating as well.

The transcription from the HIV LTR is highly dependent on the transactivator function of the tat protein. In the presence of tat, often expressed by the core packaging construct existing in producer cells, vector transcription from the HIV LTR is stimulated strongly. As that full-length "viral" RNA has a full complement of packaging signals, the RNA is encapsidated efficiently into vector particles and transferred to target cells. The amount of vector RNA available for packaging in producer cells is a rate-limiting step in the production of infectious vector.

The entire enhancer or the entire enhancer and promoter regions of the 5' LTR can be substituted with the enhancer or the enhancer and promoter of the human cytomegalovirus (CMV) or murine Rous sarcoma virus (RSv).

The high level of expression of the 5' LTR modified transfer vector RNA obtained in producer cells in the absence of a packaging construct indicates the producing vector is functional in the absence of a functional tat gene. Functional deletion of the tat gene as indicated for the packaging plasmid disclosed hereinabove would confer a higher level of biosafety to the lentiviral vector system given the number of pathogenetic activities associated with the tat protein.

Exemplary Packaging Cell Lines

Pseudotyped lentiviral or retroviral particles can be produced by introducing a defective, recombinant lentiviral genome into a packaging cell (e.g., by infection with defective retroviral particle, or by other means for introducing DNA into a target cell, such as conventional transformation techniques). The defective retroviral genome minimally contains the long terminal repeats, the exogenous nucleotide sequence of interest to be transferred, and a packaging sequence ($\phi$). In general, the packaging cell provides the missing retroviral components essential for retroviral replication, integration, and encapsidation, and also expresses a nucleotide sequence encoding the desired envelope protein. However, the packaging cell does not have all of the components essential for the production of retroviral particles. The nucleotide sequence(s) encoding the missing viral component(s) in the packaging cell can be either stably integrated into the packaging cell genome, and/or can be provided by a co-infecting helper virus.

The nucleotide sequences encoding the retroviral components and the lentiviral or retroviral RNA genome can be derived from any desired lenti- or retrovirus (e.g., murine, simian, avian, or human retroviruses). In general, the retroviral components can be derived from any retrovirus that can form pseudotyped retroviral particles with the desired envelope protein, e.g., VSV G. Where VSV G is the desired envelope protein, the retroviral components can be derived from MuLV, MoMLV, avian leukosis virus (ALV), human immunodeficiency virus (HIV), or any other retrovirus that can form pseudotyped virus with VSV G as the only envelope protein or with VSV G and a relatively small amount of retroviral envelope protein.

The present invention thus provides recombinant retroviral particles, particularly pseudotyped retroviral particles. Exemplary packaging cell lines are derived from 293, HeLa, Cf2Th, D17, MDCK, or BHK cells. Retroviral particles are preferentially produced by inducibly expressing an envelope protein of interest (e.g., a retroviral envelope or the envelope protein of vesicular stomatitis virus). Inducible expression of the envelope protein may be accomplished by operably linking an envelope protein-encoding nucleotide sequence to an inducible promoter (e.g., a promoter composed of a minimal promoter linked to at least one copy of tetO, the binding site for the tetracycline repressor (tetR) of the *Escherichia coli* tetracycline resistance operon Tn10). Expression from the inducible promoter is regulated by a transactivating factor, composed of a first ligand-binding domain that negatively regulates transcription from the inducible promoter (e.g., a prokaryotic tetracycline repressor polypeptide (tetR)). Transcription of the envelope-encoding nucleotide sequence under control of the inducible promoter is activated by a transactivator when tetracycline is absent.

The packaging cell line may comprise a first polynucleotide having an HIV genome operably linked to a first inducible promoter wherein the HIV genome is defective for cis-acting elements, for self-replication and for expression of functional Env protein; a second polynucleotide encoding a functional heterologous Env protein operably linked to a second inducible promoter; and a third polynucleotide encoding a regulatable transcriptional activator controlling transcription from the first and second inducible promoters.

In one embodiment, the first, second and third polynucleotides are contained in vectors. These polynucleotides can be contained in one or more vectors, preferably plasmid vectors. In an exemplary packaging cell line, the first polynucleotide is contained in a first plasmid vector and the second polynucleotide is contained in a second plasmid vector. The third polynucleotide encoding a regulatable transcriptional activator is exemplified herein as containing a minimal CMV immediate-early gene promoter linked to seven tandem copies of the tetR-binding site replacing the CMV promoter (BglII/BamHI fragment). As discussed herein, other viral envelopes and other indicator markers will be known to those of skill in the art for use in the present invention.

In one aspect of the invention, one or more polynucleotides encoding retroviral accessory proteins, are included as part of the first or second polynucleotide constructs, for example. Accessory proteins include vpr, vif, nef, vpx, tat, eve, and vpu.

Preferably, the transcriptional activator or transactivator can be expressed at high levels in a eukaryotic cell without significantly adversely affecting general cellular transcription in the host cell transactivator expression that is sufficient to facilitate transactivation of the inducible promoter, but that is not detrimental to the cell (e.g., is not toxic to the cell). "High Levels" can be a level of expression that allows detection of the transactivator by Western blot The transactivator can preferably be expressed in a wide variety of cell types, including mammalian and non-mammalian cells such as, but not limited to, human, monkey, mouse, hamster, cow, insect, fish, and frog cells.

The transactivator can be expressed either in vivo or in vitro, and expression of the transactivator can be controlled through selection of the promoter to which the nucleotide sequence encoding the transactivator is operably linked. For example, the promoter can be a constitutive promoter or an inducible promoter. Examples of such promoters include the human cytomegalovirus promoter IE (Boshart et al., 1985), ubiquitously expressing promoters such as HSV-Tk (McKnight et al., 1984) and β-actin promoters (e.g., the human β-actin promoter as described by Ng et al., 1985).

For example, where the transactivator is a tetR polypeptide, the inducible promoter is preferably a minimal promoter containing at least one tetO sequence, preferably at least 2 or more tandemly repeated tetO sequences, even more preferably at least 5 or more tandemly repeated tetO sequences, more preferably at least 7 tandemly repeated tetO sequences or more. The minimal promoter portion of the inducible promoter can be derived from any desired promoter, and is selected according to tet cell line in which the inducible expression system is to be used. Where the cell is a mammalian cell, a preferred minimal promoter is derived from CMV, preferably from the CMV immediate early gene 1A. In addition, other inducible promoters could be employed, such as the ecdysone-inducible promoters (Invitrogen Inc., San Diego, Calif.) or the lacZ inducible promoters.

The promoter of the transactivator can be a cell type-specific or tissue-specific promoter than preferentially facilitates transcription of the transactivator in a desired cell of tissue type. Exemplary cell type-specific and/or tissue specific promoters include promoters such as albumin (liver specific; Pinkert et al., 1987), lymphoid-specific promoters (Calame et al., 1988); in particular promoters of T-cell receptors (Winoto et al., 1989) and immunoglobulins (Banerji et al., 1983; Queen and Baltimore, 1983), neuron-specific promoters (e.g., the neurofilament promoter (Byrne et al., 1989), pancreas-specific promoters (Edlunch et al., 1985) or mammary gland-specific promoters (milk whey promoter, U.S. Pat. No. 4,873,316 and European Application Publication No. 264, 166). Promoters for expression of the transactivator can also be developmentally regulated promoters as the murine homeobox promoters (Kessel et al., 1990) or the α-fetoprotein promoter (Campes et al., 1989). The promoter can be used in combination with control regions allowing integration site independent expression of the transactivator (Grosveld et al., 1987). Preferably, the promoter is constitutive in the respective cell types. For instance, the promoter is a CMV promoter, preferably a CMV immediate early gene promoter.

Isolated Nucleic Acid-Based Vectors of the Invention

The isolated nucleic acid-based vectors of the invention, e.g., those which are not delivered in a viral particle and/or do not encode one or more viral proteins but may comprise viral transcriptional and/or translational regulatory elements, include a heterologous nucleic acid sequence of interest optionally operably linked to a regulatory nucleic acid sequence. The heterologous gene of interest in the isolated nucleic acid-based vector of the invention can be any nucleic acid of interest which can be transcribed. Generally the foreign gene encodes a polypeptide. Preferably the polypeptide has some therapeutic benefit. The polypeptide may supplement deficient or nonexistent expression of an endogenous protein in a host cell.

It may be desirable to modulate the expression of a gene regulating molecule in a cell by the introduction of a molecule by the method of the invention. The term "modulate" envisions the suppression of expression of a gene when it is over-expressed or augmentation of expression when it is under-expressed.

The method of the invention may also be useful for neuronal, glial, fibroblast or mesenchymal cell transplantation, or "grafting", which involves transplantation of transfected cells into the central nervous system or into the ventricular cavities or subdurally onto the surface of a host brain. Such methods for grafting will be known to those skilled in the art and are described in Neural Grafting in the Mammalian CNS, Bjorklund & Stenevi, eds. (1985).

For diseases due to deficiency of a protein product, gene transfer of an isolated nucleic acid-based vector of the invention could introduce a normal gene into the affected tissues for replacement therapy, as well as to create animal models for the disease using antisense mutations.

The promoter sequence of an isolated nucleic acid-based vector of the invention may be homologous or heterologous to the desired gene sequence. A wide range of promoters may be utilized, including a viral or a mammalian promoter. Cell or tissue specific promoters can be utilized to target expression of gene sequences in specific cell populations. Suitable mammalian and viral promoters for the instant invention are available in the art.

Optionally during the cloning stage, the nucleic acid construct referred to as the transfer vector also contains a selectable marker gene. Marker genes are utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate etc. and cell surface markers.

Exemplary Disorders and Genes

The invention includes the use of a vector, e.g., a lentiviral vector, comprising any open reading frame encoding a gene product useful to prevent, inhibit or treat a disorder in a mammal characterized by the lack of, or reduced levels of, that gene product. For example, the disorder may be characterized by the lack of, or reduced levels of one or more lysosomal enzymes (see, e.g., enzymes described in FIG. 5 in U.S. Pat. No. 5,798,366, the disclosure of which is specifically incorporated by reference herein). Exemplary disorders include GM1 gangliosidosis, which is caused by a deficiency in β-galactosidase; Tay-Sachs disease, a GM2 gangliosidosis which is caused by a deficiency of β-hexosaminidase A (acidic isozyme); Sandhoff disease, which is caused by a deficiency of β-hexosaminidase A & B (acidic and basic isozymes); Fabry disease, which is caused by a deficiency in α-galactosidase; Hurler-syndrome, which is caused by a deficiency of alpha-L-iduronidase, mucopolysaccharidosis type VII, which is caused by a deficiency in beta-glucuronidase, and Gaucher disease, which is a deficiency in β-glucocerebrosidase, as well as Hunter syndrome (a deficiency of iduronate-2-sulfatase); Sanfilippo syndrome (a deficiency of heparan sulfate sulfatase, N-acetylglucosamidase); Morquio syndrome (a deficiency of galactosamine-6-sulfate sulfatase or beta-galactosidase); Maroteaux-Lamy syndrome (a deficiency of arylsulfatase B); mucopolysaccharidosis type II; mucopolysaccharidosis type III (A, B, C or D; a deficiency of heparan sulfate sulfatase, N-acetyl-alpha-D-glucosaminidase, acetyl CoA:alpha-glucosaminide N-acetyl transferase or N-acetylglucosamine-6-sulfate sulfatase); mucopolysaccharidosis type IV (A or B; a deficiency of galactosamine-6-sulfatase and beta-galatacosidase); mucopolysaccharidosis type VI (a deficiency of arylsulfatase B); mucopolysaccharidosis type VII (a deficiency in beta-glucuronidase); mucopolysaccharidosis type VIII (a deficiency of glucosamine-6-sulfate sulfatase); mucopolysaccharidosis type IX (a deficiency of hyaluronidase); Tay-Sachs disease (a deficiency in alpha subunit of beta-hexaminidase); Sandhoff disease (a deficiency in both alpha and beta subunit of beta-hexosaminidase); GM1 gangliosidosis (type I or type II); Fabry disease (a deficiency in alpha galactosidase); metachromatic leukodystrophy (a deficiency of aryl sulfatase A); Pompe disease (a deficiency of acid maltase); fucosidosis (a deficiency of fucosidase); alpha-mannosidosis (a deficiency of alpha-mannosidase); beta-mannosidosis (a deficiency of beta-mannosidase), ceroid lipofuscinosis, and Gaucher disease (types I, II and III; a deficiency in glucocerebrosidase), as well as disorders such as Hermansky-Pudlak syndrome; Amaurotic idiocy; Tangier disease; aspartylglucosaminuria; congenital disorder of glycosylation, type Ia; Chediak-Higashi syndrome; macular dystrophy, corneal, 1; cystinosis, nephropathic; Fanconi-Bickel syndrome; Farber lipogranulomatosis; fibromatosis; geleophysic dysplasia; glycogen storage disease I; glycogen storage disease Ib; glycogen storage disease Ic; glycogen storage disease III; glycogen storage disease IV; glycogen storage disease V; glycogen storage disease VI; glycogen storage disease VII; glycogen storage disease 0; immunoosseous dysplasia, Schimke type; lipidosis; lipase b; mucolipidosis II; mucolipidosis II, including the variant form; mucolipidosis IV; neuraminidase deficiency with beta-galactosidase deficiency; mucolipidosis I; Niemann-Pick disease (a deficiency of sphingomyelinase); Niemann-Pick disease without sphingomyelinase deficiency (a deficiency of npc1, a cholesterol metabolizing enzyme); Refsum disease; Sea-blue histiocyte disease; infantile sialic acid storage disorder; sialuria; multiple sulfatase deficiency; triglyceride storage disease with impaired long-chain fatty acid oxidation; Winchester disease; Wolman disease (a deficiency of cholesterol hydrolase); Deoxyribonuclease I-like 1 disorder; arylsulfatase E disorder; ATPase, H+ transporting, lysosomal, subunit 1 disorder; glycogen storage disease IIb; Ras-associated protein rab9 disorder; chondrodysplasia punctata 1, X-linked recessive disorder; glycogen storage disease VIII; lysosome-associated membrane protein 2 disorder; Menkes syndrome; congenital disorder of glycosylation, type Ic; and sialuria. In particular, the invention is useful to prevent, inhibit or treat lysosomal storage diseases wherein the lysosomal enzyme is trafficked to the lysosome (within the cell and between cells) by specific glycosylation.

For instance, Tay-Sachs disease results from mutations in the HexA gene, which encodes the alpha subunit of β-hexosaminidase, leading to a deficiency in the A isoenzyme. The A isoenzyme is responsible for the degradation of GM2 ganglioside. When this enzyme is deficient in humans, GM2 ganglioside accumulates progressively and leads to severe neurological degeneration. In the mouse model of Tay-Sachs disease (generated by the targeted disruption of the HexA gene) (Sandhoff et al., 1989), the mice store GM2 ganglioside in a progressive fashion, but the levels never exceed the threshold required to elicit neurodegeneration. In the mouse (but not in a human) a sialidase is sufficiently abundant that it can convert GM2 to GA2 (asialo ganglioside 2), which can then be catabolized by the hexosaminidase B isoenzyme.

Gaucher disease is the name given to a group of lysosomal storage disorders caused by mutations in the gene that codes for an enzyme called glucocerebrosidase ("GC"). Gaucher disease is caused by deficiency of GC. All of the mutations in the gene alter the structure and function of the enzyme which lead to an accumulation of the undegraded glycolipid substrate glucosylceramide, also called glucocerebroside, in cells of the reticuloendothelial system. Each particular mutation of the human GC gene leads to a clinical disease collectively known as Gaucher disease. These disorders are usually classified into three types: type 1 (non-neuronopathic), type 2 (acute neuronopathic) and type 3 (subacute neuronopathic), the type depending on the presence and severity of neurologic involvement.

GC is a monomeric, membrane-associated, hydrophobic glycoprotein with a molecular weight of 65,000 daltons. Human GC contains 497 amino acids and is translated as a precursor protein with a 19 amino acid hydrophobic signal peptide which directs its co-translational insertion into the lumen of the endoplasmic reticulum-golgi-lysosome complex as reported by Erickson et al. (1985). GC acts at the acidic pH of the lysosome to hydrolyze beta-glucosidic linkages in complex lipids ubiquitously found in all membranes to form the byproducts of glucose and ceramide. The catalytic activity of GC is increased in vitro by detergents, lipids, and in vivo by a naturally occurring activator known as sphingolipid activator protein-2 (SAP-2 or saposin C). See, Ho et al. (1971); O'Brian et al. (1988). While more than twenty mutations in the human GC gene are known, only two are common. See, Tsuji et al. (1988). The two common mutations account for approximately 70% of the mutant alleles, as reported by Firon et al. (1990). Mutant GC genes code for aberrant proteins that are either catalytically altered or unstable and rapidly disappear from the cell.

Although GC is deficient in all of a subject's cells, for unknown reasons, the accumulation of the substrate glucosylceramide occurs virtually only in macrophages. To correct the enzyme deficiency in macrophages, two approaches have been used. The first treatment is based allogeneic bone marrow transplantation, which results in the repopulation of affected tissues with enzyme-competent macrophages. See, Rappeport et al. (1986). The second approach to treatment which has resulted in clinical improvement in Gaucher disease patients is macrophage-targeted enzyme replacement. This treatment takes advantage of naturally occurring mannose receptors on macrophages and the exposition of accessible mannose receptors in the oligosaccharides of glucocerebrosidase to efficiently deliver the enzyme to macrophages. See, Barranger (1989); Takasaki et al. (1984); and Furbish et al., (1981). However, allogeneic bone marrow transplantation has associated with it morbidity and mortality risks that are unacceptable for many patients. Further, HLA matched bone marrow donors do not exist for the majority of patients. As for macrophage-targeted enzyme replacement, it is currently an expensive and life-long therapy.

Hurler syndrome is an autosomal recessive disease resulting from deficient alpha-iduronidase enzymatic activity and the consequent systemic accumulation of glycosaminoglycan (GAG) substrates. The disease is characterized by hepatosplenomegaly, severe skeletal involvement, progressive mental retardation, and is typically lethal in childhood.

To be an effective permanent treatment for any disease capable of being treated by gene therapy, the transfer and sustained expression of genes in cells important to the pathogenesis of the particular disease is required. Sufficient and long term expression of a transduced gene in the progeny of transduced cells, e.g., transduced stem cells such as pluripotent bone marrow stem cells, for example, using a lentivirus, could correct the deficiency of the enzyme in many if not all relevant cell types.

Dosages, Formulations and Routes of Administration of the Agents of the Invention The therapeutic agents of the invention are preferably administered so as to achieve beneficial results. The amount administered will vary depending on various factors including, but not limited to, the agent chosen, the disease, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., *Immunity*, 3, 165 (1995); Stevenson et al., *Immunol. Rev.*, 145, 211 (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)). Pharmaceutical formulations, dosages and routes of administration for nucleic acids are generally disclosed, for example, in Felgner et al., supra. Nucleic acid molecules may be complexed with polyethyleneimine, polylysine or cationic lipids such as DOTMA, DOTAP, DOGS, or DC-Chol (N-(1-[2,3-dioleoyloxy]propyl)-N,N,N-trimethylammonium chloride, DOTAP; N-(1-[2,3-dioleyloxy]propyl)-N,N,N-trimethylammonium chloride, DOTMA; 3β-[N—(N',N'-Dimethylaminoethane)-carbamoyl]Cholesterol, DC-Chol) In one embodiment, DNA is delivered under pressure into the hepatic circulation.

The amount of therapeutic agent administered is selected to treat a particular indication. The therapeutic agents of the invention are also amenable to chronic use for prophylactic purposes, preferably by systemic administration.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the therapeutic agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient hereof The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenevinyl alcohol copolymers, ethylene-vinyloxyethanol copolymers; silicone copolymers, for example, polysiloxane-polycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane-copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other therapeutic agents.

The invention is further described by the following non-limiting examples.

Example I

Materials and Methods

Production and concentration of lentiviral vector. The lentiviral vector was generated from a first-generation tetracycline-inducible VSVG-pseudotyped lentiviral packaging cell line SODk1-CGFI (Kafri et al., 1999). The vector (HR'cmvGFP) contained a humanized red-shift GFP gene driven by a human cytomegalovirus immediate-early promoter. The vector producer cells were maintained in Dulbecco's modified Eagle's medium (DMEM) (Life Technologies, Inc., Gaithersburg, Md.) containing 10% tetracycline-free FCS (Clontech, Palo Alto, Calif.) and 0.7 µg/ml doxycycline (Sigma, St. Louis, Mo.). Induction of cells was initiated by splitting cells into polylysine (0.01% solution; Sigma) pre-coated plates in the absence of doxycycline. The cells were washed twice with PBS (Life Technologies Inc.) and fed daily with doxycycline-free medium containing 5 mM sodium butyrate (Sigma). Vector-containing medium was collected 3 and 4 days after induction and filtered through a 0.2 µm pore filter. The vector stocks were further concentrated by ultracentrifugation at 50,000 g for 2 hours (Beckman SW-28 rotor), followed by resuspending and incubating at 37° C. for 2 hours in $\frac{1}{200}$ of starting volume of Tris-buffered saline (TBS, pH 7.8) containing 10 mM $MgCl_2$ dNTPs (0.1 mM each), 3 mM spermine, and 0.3 mM spermidine. After a second ultracentrifugation at 50,000 g for 30 minutes (Beckman TLA-100.3 rotor), the vector pellet was resuspended in $\frac{1}{2000}$ of the initial volume of TBS with 2 µg/ml Polybrene and was stored at −80° C.

Titration assay for vector potency. Human 293 embryonic kidney cells or murine NIH 3T3 cells were subcultured into six-well culture plates (Beckton Dickinson, Franklin Lakes, N.J.) at $10^5$ cells/well with DMEM containing 10% FBS (Life Technologies Inc.). After 8 hours had passed, cells were exposed to serial dilution of vector stocks in the presence of Polybrene (8 µg/ml). Titers were scored 48 hours after transduction by FACS analysis to quantitate GFP-expressing cells. All assays were done in triplicate.

In vivo vector administration to mice. Thirty-one 8 week-old normal BALB/c mice (15 male, 16 female) were obtained from Charles River Laboratories (Wilmington, Mass.) and housed in a pathogen-free facility on a 12-hour light/dark cycle. One week later, the mice were randomly divided into control (7 male, 7 female) and treated groups (8 male, 9 female). The treated groups were injected i.v. with 100 µl pooled concentrated vector stock into the tail vein over 3-6 seconds; the control groups were injected with 100 µl TBS containing 2 µg/ml Polybrene. All animal procedures were done under aseptic conditions and in accordance with protocols approved by the Institutional Animal Care and Use Committee. Mice were periodically bled by the retro-orbital technique.

Perfusion and organ collection. At either 4 or 40 days after injection, the mice were euthanized by intraperitoneal administration of an overdose of sodium nembutal (Abbott Laboratories). Each mouse was perfused transcardially through the aorta with PBS for 5-10 minutes until its liver turned pale, followed by perfusion with 4% formaldehyde-PBS for 10-15 minutes. Nine organs were removed in the following order: gonad, bladder, gastrointestinal tract, lung, heart, kidney, liver, spleen, and brain. Organs were post-fixed in 4% formaldehyde-PBS for 0.5 to 2 hours, and then transferred into a 30% sucrose-PBS solution for storage at 4° C. until further processing. Bone marrow was harvested in PBS from femur and tibia of each mouse, and stored in Cell Lysis Solution (Puregene, Minneapolis, Minn.) for further DNA isolation. The remains of mice were stored in 4% formaldehyde-PBS for pathologic analysis. Aliquots of each organ were segregated for two different assays. Genomic DNA was isolated from the first aliquot using a DNA isolation kit (Puregene) for quantitation of GFP gene. The second aliquot was immersed in 10% neutral-buffered formalin for 1-3 days and embedded in paraffin by routine methods. Sections of 4 to 6 μm, stained with H&E, were examined.

Real-time QPCR using concurrent reactions. Both GFP transgene and endogenous mouse Apob sequence (as an internal control) were quantitated simultaneously in the same reaction well of a total 50 μl PCR volume by real-time PCR. The TaqMan probe for detection of GFP transgene was labeled with fluorescent reporter dye 6FAM at the 5' end and quencher dye TAMRA at the 3' end (5'-CCGACAAGCA-GAAGAACGGCATCA-3'; SEQ ID NO:1), whereas the probe for Apob was labeled with fluorescent reporter dye VIC at the 5' end and quencher dye TAMRA at the 3' end (5'-CCTTGAGCAGTGCCCGACCATTC-3'; SEQ ID NO:2). Sequences of TaqMan primer-probe sets for GFP (sense, 5'-ACTACAACAGCCACAACGTCTATATCA-3'; SEQ ID NO:3; antisense, 5'-GGCGGATCTTGAAGTTCACC-3'; SEQ ID NO:4) and Apob (sense, 5'-CGTGGGCTCCAG-CATTCTA-3'; SEQ ID NO:5; antisense, 5'-TCACCAGT-CATTTCTGCCTTTG-3'; SEQ ID NO:6) were designed using the Primer Express program (PE Applied Biosystems, Foster City, Calif.). The duplex reaction contained 0.01-1 μg genomic DNA, 200 nM of each GFP primer, 200 nM GFP probe, 40 nM of each Apob primer, 200 nM Apob probe, and 25 μl TaqMan 2× Universal Master Mix (PE Applied Biosystems) including 8% glycerol, 1× TaqMan buffer A, 5 mM MgCl$_2$, 400 μM dUTP, 200 μM dATP, dCTP, AND dGTP (each), AmpliTaq Gold (0.025 U/μl), and AmpErase UNG (0.01 U/μl). All PCR reactions were set up in a MicroAmp Optical 96 well Reaction Plate (PE Applied Biosystems). Amplification conditions were 2 minutes at 50° C. and 10 minutes at 95° C. for the first cycle, followed by 50 cycles of 95° C. for 15 seconds and 60° C. for 1 minute. The TaqMan probes were cleaved during amplification, generating specific fluorescence emission for the FAM-labeled GFP probe or the VIC-labeled Apob probe. The data were collected in real time from the ABI PRIME 7700 Sequence Detector and transferred online to a Macintosh 7100 for analysis using the Sequence Detector version 1.6 program (PE Applied Biosystems). Unknown samples were run in triplicate, and standard samples were in duplicate. All threshold cycle (Ct) values of GFP transgene were normalized by Ct of Apob that measured the total DNA content in each individual reaction. Transgene frequencies of unknown samples were interpolated from a standard curve (ranging from 0.001% to 100%) that was established by simultaneous amplification of a series of genomic DNA mixtures derived from a mouse myeloid cell line (32Dp210) (Carlesso et al., 1994) and a GFP-containing cell line (32Dp210-LNChRGFP) with 1 copy per genome (as determined by Southern blot analysis).

Flow cytometry. Blood samples were collected using heparinized hematocrit tubes and diluted 1:1 into heparin sodium solution (ICN Biomedicals Inc., Aurora, Ohio). PBL were fixed in Optilyse B solution (Immunotech, Marseille, France), while red cells were further lysed by the addition of dH$_2$O. Specific subsets of mouse PBL were detected by staining with PE-conjugated hamster monoclonal antibody to mouse CD3e for T lymphocytes (Pharmingen, San Diego, Calif.), or PE-conjugated rat monoclonal antibody to mouse CD45R/B220 for B lymphocytes (PharMingen). PE-conjugated Armenian hamster immunoglobulin group 1 and rat immunoglobulin G2a were used, respectively, as isotype controls. Cultured cells were trypsinized, then fixed in 4% formaldehyde, and diluted in PBS to a concentration of 5×10$^5$ cells/ml. Two-color FACS analysis for cellular GFP (FL-1) and PE staining (FL-2) were carried out by FACSCalibur with the CellQuest program (Becton Dickinson). Cells from mice injected with TBS were analyzed as negative controls for GFP expression in blood samples. For titration assays, human 293 cells or mouse 3T3 cells were used as negative controls; whereas uninduced SODk1-CGFI packaging cells were used as positive controls.

Immunohistochemical staining for GFP-expressing cells. After several PBS rinses and an incubation in 3% hydrogen peroxide, the fixed cryosections were blocked in 5% normal goat serum (Vector Labs, Burlingame, Calif.). The sections were then incubated with the primary anti-GFP antibody (1:50; Clontech Lab) in 5% goat serum-0.1% Triton X-100 overnight at 4° C. After rinsing, the sections were incubated in the biotinylated rabbit anti-goat secondary antibody (Vector Labs) for 1 hour, washed three times with PBS, stained with biotinylated horseradish peroxidase-avidin (ABC kit; Vector Labs), and then colorized by using a diaminobenzidine (DAB) substrate kit (Vector Labs). After staining, sections were washed in dH$_2$O, air-dried, and mounted in Permount (Fisher Scientific Co., Fairlawn, N.J.).

Results

Vector Concentration and Administration

To assess the potency of the first-generation lentiviral vector HR'cmvGFP, vector stocks from several batches of inductive production and concentration were thawed at 30° C. and pooled. Transduction was evaluated with both human 293 cells and mouse NIH 3T3 cells by FACS analysis for GFP expression (Table 1). Up to 780-fold increase in titer was observed in concentrated vector supernatants, resulting in 1.8±0.15×10$^8$ transforming units (TU) per milliliter. Titers obtained from human 293 cells were always about 10-fold higher than those from mouse NIH 3T3 cells. Thus, about 2×10$^7$ 293 TU of recombinant HIV-GFP (in 100 μl) was injected through the tail vein into each of 17 normal BALB/c mice.

TABLE 1

Potency of lentiviral vector generated from packaging cell line

| | Titer* determined by FACS analysis for GFP expression (TU/ml) | | | |
|---|---|---|---|---|
| | Before concentration | | After concentration | |
| Cells | Mean | SD | Mean | SD |
| Human 293 | 2.3 × 10$^5$ | ±0.87 × 10$^5$ | 1.8 × 10$^8$ | ±0.15 × 10$^8$ |
| Murine NIH 3T3 | 2.6 × 10$^4$ | ±0.12 × 10$^4$ | 1.2 × 10$^7$ | ±0.76 × 10$^7$ |

*Vector-containing supernatants were stored at −70° C. and thawed in 30° C. water-bath before titration assay.

Pathology

To evaluate toxicity due to the i.v. administration of VSVG-pseudotyped lentiviral vector, hematoxylin and eosin (H&E)- stained sections from 17 treated and 12 control mice were examined by light microscopy (Table 2). Mucosal and submucosal edema was found in the gastrointestinal tract of 14 treated and 6 control mice, and congestion was observed in the livers of both control and treated mice. These changes appear to have resulted from the perfusion and fixation procedure. One mouse (F11) developed a brain abscess, presumed to be the result of injury from the blood collection procedure. Lymphocyte infiltration or other signs of inflammation were not observed in any of the examined organs. Thus, no significant lesions attributable to the test article were found in any of the tissues.

reaction conditions, amplifications of GFP were compared with same well Apob from a serial dilution (>5-log-fold) of a reference cell preparation, that is, cells containing one copy of GFP per cell. Theoretically, if the reaction efficiencies for both genes were the same and constant across various concentrations of DNA template, the difference in amplifications between the two targets should remain constant. This proved to be true, as indicated by the two parallel amplification curves for GFP and Apob, and further confirmed by graphing the difference in threshold cycle numbers (ΔCt) against the log of the DNA dilution fold. Regression analysis of these data demonstrated a horizontal line with a negligible slope

TABLE 2

Pathological findings of treated and control animals

| Mouse | Number | Liver | Spleen | Lung | Heart | Kidney | Brain | GI tract | Gonad | Skin* |
|---|---|---|---|---|---|---|---|---|---|---|
| | | | | 4 Days post-administration | | | | | | |
| Control | ConM1 | NSL | NSL | NSL | NSL | NSL | NSL | — | NSL | NSL |
| | ConM3 | NSL | — | NSL | NSL | NSL | NSL | edema | NSL | — |
| | ConF4 | Cong | NSL | — | — | — | — | edema | — | NSL |
| | ConF5 | — | — | NSL | NSL | NSL | NSL | NSL | NSL | — |
| | ConF6 | NSL | NSL | NSL | NSL | NSL | NSL | edema | NSL | NSL |
| Treated | TrM12 | NSL | NSL | NSL | NSL | NSL | NSL | edema | — | — |
| | TrM13 | NSL | NSL | NSL | NSL | NSL | NSL | NSL | NSL | — |
| | TrM14 | NSL | NSL | NSL | NSL | NSL | NSL | edema | NSL | NSL |
| | TrF13 | NSL | NSL | NSL | NSL | NSL | NSL | edema | NSL | — |
| | TrF14 | NSL | NSL | NSL | NSL | NSL | NSL | edema | NSL | NSL |
| | TrF15 | NSL | NSL | NSL | NSL | NSL | NSL | edema | NSL | NSL |
| | | | | 40 Days post-administration | | | | | | |
| Control | ConM5 | Cong | NSL | Hemo | NSL | NSL | NSL | edema | — | NSL |
| | ConM6 | NSL | NSL | NSL | NSL | NSL | NSL | NSL | NSL | — |
| | ConM15 | NSL | NSL | NSL | NSL | NSL | NSL | edema | NSL | — |
| | ConF1 | NSL | NSL | NSL | NSL | NSL | NSL | edema | — | NSL |
| | ConF2 | NSL | NSL | NSL | NSL | NSL | NSL | NSL | NSL | NSL |
| | ConF3 | NSL | NSL | NSL | NSL | NSL | NSL | NSL | — | — |
| | ConF16 | NSL | NSL | NSL | NSL | NSL | NSL | NSL | NSL | — |
| Treated | TrM7 | Cong | NSL | NSL | NSL | NSL | NSL | edema | NSL | — |
| | TrM8 | Cong | NSL | NSL | NSL | NSL | NSL | edema | NSL | — |
| | TrM9 | NSL | NSL | NSL | NSL | NSL | NSL | edema | NSL | — |
| | TrM10 | Cong | NSL | NSL | NSL | NSL | NSL | edema | — | NSL |
| | TrM11 | NSL | NSL | NSL | NSL | NSL | NSL | edema | NSL | — |
| | TrF7 | NSL | NSL | NSL | NSL | NSL | NSL | NSL | — | NSL |
| | TrF8 | NSL | NSL | NSL | NSL | NSL | NSL | edema | NSL | — |
| | TrF9 | Cong | NSL | NSL | NSL | — | NSL | edema | — | NSL |
| | TrF10 | NSL | NSL | NSL | — | NSL | NSL | edema | NSL | — |
| | TrF11 | NSL | NSL | NSL | NSL | NSL | abscess | NSL | edema | — |
| | TrF12 | Cong | NSL | — | — | — | — | edema | — | — |

NSL, no significant lesions were found.
Cong, small foci of sinusoidal congestion.
Hemo, small foci of extravasation of blood.
Edema, mucosal and submucosal edema due to perfusion and fixation procedures.
—, Not examined.
*Tail was examined at the injection site.

Duplex Real-Time PCR for GFP and Apob

To achieve a high degree of sensitivity, reproducibility, and accuracy in quantitating gene transfer efficiency, a real-time QPCR assay was established for concurrent quantification of GFP and endogenous mouse apolipoprotein B (Apob) in a single reaction vessel. The amplification plots for GFP shift to the right as initial transgene input is reduced (from 100% to 0.001%) white same-well Apob amplifications remain constant because total DNA content is similar in all samples (that is, 1 μg/well as determined by spectrophotometry). A common threshold was selected in the exponential phase of PCR reactions to determine a specific threshold cycle number for each sample.

To determine whether the concurrent amplification of GFP and Apob in the same well was occurring under optimized (0.04). This result indicated that the PCR efficiency for GFP was comparable to that for Apob in this duplex reaction system, thus confirming that concurrent amplification of Apob would serve as a reliable internal reference against which to normalize GFP measurements.

To evaluate further the sensitivity, accuracy, and reproducibility of this real-time QPCR assay, standard curves were established by plotting normalized threshold cycle number (nor CT) against transgene frequency using a set of standard samples. Although each of the standards contained a different percentage of GFP transgene, the total concentration of DNA remained similar. When Ct was normalized for DNA concentration on the basis of equal optical density (OD) readings using a spectrophotometer, the linear regression analysis of the curve indicated a slope of −4.02, with $r^2$ of 0.984. An even higher squared correlation coefficient (0.999) was observed in standard curve using the same set of samples when normalizing Ct-GFP with in-well Apob readings. These results indicate an extremely efficient quantitation assay that remains linear (5-log fold) from 100% to 0.001% transduced cells. Considering that 1 μg DNA is equivalent to about $10^5$ cells, this assay can detect as few as one copy of GFP per reaction. Moreover, there was a high reproducibility of this real-time QPCR. A "mean standard curve" was generated by analyzing norCt values derived from 20 PCR reactions (amplified in 10 separate runs) of the same set of samples. The standard deviation was <3% of nor Ct for each of the standard samples, suggesting a stable high reproducibility over the 5-log-fold quantitation.

days after injection (Table 3). Relatively high levels of GFP were observed in liver (ranging from 0.3 to 1.3%) and spleen (ranging from 0.045 to 0.38%), which were substantially lower than those in mice 4 days after injection. Gonads from all but one treated animal (TrF9) contained undetectable to barely detectable levels of GFP (<9 copies GFP per $10^5$ cells). From undetectable to 0.30% transgene was found in other organs. Remarkably, very high levels of transgene (4.7-22.7%) were observed in bone marrow from all but one mouse. These levels are comparable to those observed in mice 4 days after treatment. These results suggested that bone marrow might be the organ most accessible to VSVG-pseudotyped lentiviral vector.

TABLE 3

Tissue distribution of GFP in mice 40 days after vector injection (%)

| Mouse | Number | Gonad | Bladder | GI tract | Brain | Kidney | Heart | Lung | Spleen | Liver | BM |
|---|---|---|---|---|---|---|---|---|---|---|---|
| | | | | | Male | | | | | | |
| Control | ConM4 | UD | 0.027 | UD | na | na | UD | UD | UD | UD | UD |
| | ConM6 | UD | UD | UD | UD | UD | UD | UD | UD | 0.02 | UD |
| | ConM15 | UD | UD | UD | 0.003 | UD | 0.002 | UD | UD | UD | na |
| Treated | TrM7 | 0.005 | 0.037 | UD | 0.061 | UD | na | UD | 0.267 | 0.639 | 17.94 |
| | TrM8 | 0.008 | 0.087 | 0.002 | 0.161 | 0.002 | 0.043 | UD | 0.137 | 0.550 | na |
| | TrM9 | 0.003 | 0.060 | 0.004 | UD | 0.001 | 0.015 | UD | 0.235 | 0.468 | 13.56 |
| | TrM10 | 0.003 | 0.022 | UD | 0.007 | 0.002 | 0.023 | 0.003 | 0.202 | 0.762 | na |
| | TrM11 | UD | 0.040 | UD | 0.023 | 0.003 | 0.077 | 0.304 | 0.045 | 1.263 | 14.54 |
| | | | | | Female | | | | | | |
| Control | ConF3 | UD | UD | UD | UD | UD | na | 0.005 | UD | UD | UD |
| | ConF4 | 0.003 | na | UD | 0.003 | UD | UD | 0.001 | UD | UD | na |
| | ConF16 | UD | UD | UD | UD | UD | UD | UD | UD | 0.01 | UD |
| Treated | TrF7 | 0.006 | na | UD | 0.005 | UD | 0.003 | 0.073 | 0.289 | 0.256 | na |
| | TrF8 | 0.006 | 0.066 | UD | UD | UD | 0.001 | 0.002 | 0.183 | 0.713 | 4.743 |
| | TrF9 | 0.034 | 0.058 | UD | 0.053 | 0.003 | 0.007 | 0.008 | 0.166 | 0.878 | 7.895 |
| | TrF10 | UD | 0.202 | UD | 0.014 | 0.02 | UD | 0.060 | 0.072 | 1.292 | 15.12 |
| | TrF11 | 0.009 | UD | 0.001 | 0.111 | 0.001 | 0.022 | 0.026 | 0.132 | 0.969 | 0.208 |
| | TrF12 | na | 0.846 | UD | 0.102 | 0.003 | UD | 0.003 | 0.377 | 0.728 | 22.68 |

UD, un-detectable.
na, not available.

Biodistribution of GFP Transgene 4 Days After Administration

To assess where, and to what degree, the HIV-based GFP-containing lentiviral vector localized within the animals shortly after vector administration, 10 different organs were carefully collected from six treated and six control mice 4 days after injection. Mice were perfused transcardially for 20 minutes to minimize potential DNA contamination from blood. Cross sections of each organ were examined for GFP transgene by real-time QPCR assay. High levels of GFP were observed in bone marrow (ranging from 5 to 37 GFP copies per 100 genome equivalents), liver (12-59), and spleen (20-54) in treated mice. In contrast, transgene was undetectable in the brain of one animal and the gastrointestinal tract of all treated mice. Various amounts of transgene were obtained in other organs from all treated animals, ranging from 0.01 to 1 GFP copy per 100 genome equivalents. These observations demonstrated a variable distribution of in vivo-transduction capability of lentiviral vectors.

Biodistribution of GFP Transgene 40 Days After Administration

To assess stably transduced transgene efficiency in treated mice, organ distribution of GFP was determined in mice 40

Transgene Frequency in Peripheral Blood Leukocytes

To monitor the transgene in blood cells, whole blood was collected periodically on days 4, 11, 25, and 40 after injection and analyzed by real-time QPCR. GFP transgene frequency in peripheral blood leukocytes (PBL) decreased significantly (P<0.0001) from a mean of 0.77% (±0.27) on day 4 to 0.07% (±0.04) on day 11. Interestingly, the GFP level increased back to 0.73% (±0.47) on day 25, a comparable result to that on day 4 (P=0.858). Remarkably, it continued to increase to a level of 20.8% (±17.1) on day 40 following injection (P<0.002), indicating the presence of an additional source for GFP+leukocytes. This latter result is consistent with the earlier observation of high levels of GFP transgene in bone marrow from mice assayed 40 days after injection.

Transgene Expression in PBL by FACS Analysis

To determine whether the genetically translated GFP is biologically active, GFP expression and the murine B-cell or T-cell subsets were analyzed by two-color flow cytometry with phycoerythrin (PE) conjugates in whole blood collected periodically. FACS analysis failed to identify GFP-expressing cells in PBL on days 4, 11, and 25, although low levels of GFP transgene were detected by real-time PCR (<1%). However, up to about 10% of leukocytes were found to be GFP+in mouse TrM7, whose blood contained the highest level of transgene (62.7%) 40 days after injection. Moreover, GFP-expressing cells included both CD45R/B220+ B cells and CD3e+ T cells.

Transgene Expression in Liver Visualized by Immunochemical Staining

To characterize transduced cell type(s) further, mouse livers were studied that had relatively high levels of gene transfer by QPCR by immunochemical staining for GFP+ cells. In livers 4 days after injection (with 12-59% transgene frequency), the GFP+ cells (reddish-brown staining in cytoplasm) were most likely to be hepatocytes adjacent to blood vessels. However, no identifiable GFP+ cells were detected in liver derived from mice 40 days after injection; approximately 1% transgene frequency was measured by real-time QPCR (Table 3).

Discussion

With >300 phase I/II clinical trials conducted worldwide over the last decade, gene therapy represents one of the fastest growing areas in experimental medicine (Romano et al., 2000). Tissue biodistribution is an important aspect of characterizing new vectors, one that has received great attention from the FDA and the National Institute of Health's (NI) Recombinant Advisory Committee (FDA, 1991; FDA, 1998; Pilaro et al., 1999). However, only limited data are available from preclinical effectiveness and toxicity studies needed to evaluate these new products (Verdler et al., 1999). HIV-based lentiviral vectors are promising tools for in vivo gene therapy, but their safety issues are more critical because of their origins. Although gene transfer and transgene expression of VSVG-pseudotyped HIV-based vectors have been demonstrated by several groups in various organs (Naldini et al., 1996; Kafri et al., 1997; Johnson et al., 2000; Miyoshi et al., 1997; Woods et al., 2001), the biodistribution and systemic effects have not been assessed. In this study, the organ biodistribution and general toxicity of a first-generation lentiviral vector after tail-vein injection in mice was assessed. A real-time QPCR assay was established with a broad range of quantitation (5-log fold) to detect as few as one copy of GFP per $10^5$ cell genomes. Such studies are crucial in understanding both the potential efficacies, as well as the level of risk for germline transmission (Pilaro et al., 1999). The unexpected observation of high bone marrow transgene frequency (ranging from 0.21 to 22.7% of total bone-marrow genome) has important implications for stem cell gene therapy.

Accurate quantitation of gene transfer (or gene correction) has been a universal challenge to the field of gene therapy. High sensitivity and reproducibility of such assays are key requirements for a successful biodistribution study, especially when extremely low gene transfer is anticipated in some of the nontarget organs such as gonad (Gordon, 1998). PCR-based DNA analysis has been specified as an adequate method in biodistribution studies by the FDA (Pilaro et al., 1999). A major impediment to the use of PCR as a quantitative technique has been the inherent change in kinetics of the chemical reaction over time as substrates and other essential components are consumed (Orlando et al., 1998). With a given PCR cycle number (for example, 25 cycles), PCR amplifications from different amounts of initial target templates could be at different stages (geometric, linear, and plateau phases) with divergent amplification rates and efficiencies. Therefore, conventional end-point CR methods are limited by the sensitivity of detection in both linear and plateau phases of the PCR. However, a systemic biodistribution study of gene transfer frequency demands the capability to quantitate target templates over several-log fold.

A new technique for quantitating PCR products in real time has been developed recently (Held et al., 1996; Becker et al., 1999). It is able to identify and measure amplification signals in "real time" (that is, every 7 seconds) during PCR reactions. The real-time QPCR assay established here could measure as few as one copy of target sequence in a background of about $10^5$ genomes (1 μg DNA). Moreover, reproducibility and accuracy were consistently high over a wide range of quantitation, with 5-log-fold difference in the amount of target templates (1 to $10^5$ copies). In addition, the assay was further optimized by simultaneously quantitating both target GFP sequence and internal-control Apob sequence in the same reaction. In each reaction well, the amplification of Apob serves as an internal reference to validate each reaction mixture (an extremely important issue when the target sequence is very low or undetectable). Such a modification also has the advantage of reducing sampling and other systemic errors, and eliminates the need for a second set of control reactions. Thus, it is more accurate and economical.

Wild-type vesicular stomatitis virus (VSV) has a broad host range extending from insects to nearly all mammals (Schnitzlein et al., 1985). In humans, VSV infections result in nonsevere influenza-like symptoms (Fields et al., 1967). The VSV glycoprotein G is the major antigenic determinant responsible for virus attachment and membrane fusion (Coll, 1995). Unlike most viral envelope proteins, which must bind to a specific cell-surface protein receptor to mediate infection (Albritten et al., 1989; Sattenau et al., 1986), VSVG interacts with an intrinsic phospholipid component of the plasma membrane (Mastromanno et al., 1987; Knoieczko et al., 1994). Moreover, the VSVG also has the unique ability to withstand the shearing forces encountered during ultracentrifugation. Therefore, to broaden the target cell range and increase potency in vector preparations, VSVG has been utilized to "pseudotype" gene therapy vectors such as retroviral (Burns et al., 1993), HIV-1-based (Naldini et al., 1996), and FIV-based (Poeschla et al., 1998) lentiviral vectors.

In vitro studies on VSVG-pseudotyped HIV-1-based vectors have demonstrated efficient gene transfer into nondividing airway epithelial cells (Goldman et al., 1997), unstimulated primary T lymphocytes (Costello et al., 2000), non-prestimulated CD34+cells (Douglas et al., 1999), terminally differentiated macrophages, and peripheral blood monocyte-derived dendritic cells (Schroers et al., 2000). By route of local administration, in vivo gene delivery has been accomplished in rat brain (Naldini et al., 1996; Blomer et al., 1997), in liver and muscle (Kafri et al., 1997), in retina (Mixoshi et al., 1997), and in airway epithelia (Johnson et al., 2000). In this study, overall in vivo organ distribution was assessed by injecting a low dose of lentivirus i.v. into mice ($2 \times 10^7$ IU/mouse). Relatively high gene transfer was observed in bone marrow (ranging from 0.21 to 22.7% transgene frequency), liver (0.26-1.3%), and spleen (0.045-0.38%) from mice 40 days after injection. Variable low levels of transgene were observed in bladder (from undetectable to 0.85%), lung (from undetectable to 0.30%), heart (from undetectable to 0.021%), brain (from undetectable to 0.16%), kidney (from undetectable to 0.003%), and gastrointestinal tract (from undetectable to 0.004%). These observations do not conflict with those observed by others (Park et al., 2000), in which a relatively high dose of lacZ-containing lentivirus ($1 \times 10^8$ TU) was injected into the portal vein of mice. The expression of β-galactosidase was detected by X-gal staining in liver (0.16±0.08% of hepatocytes) and spleen, but not in the brain, heart, lung, kidney, and duodenum.

The GFP transgene frequency was surprisingly high in liver (up to 59%) and spleen (up to 54%) from mice 4 days after injection, and decreased dramatically to a maximum of only 1.3% in liver and 0.38% in spleen from mice 40 days after injection. This change may be due to the existence of abundant defective vector particles that contain partial reverse transcripts, and the loss of extrachromosomal proviral DNA. It has been reported that only 0.1-1% of the virus particles in VSVG-pseudotyped lentiviral vector preparations were infectious, when using the minus strong-stop cDNA fragment that was present in viral capsids as template for real-time QPCR (Scherr et al., 2001). Therefore, in this study about $2 \times 10^{11}$ particles were injected into each mouse, with about $2 \times 10^7$ transduction units. Varied partial reverse-transcription (RT) intermediates have been found to be present in newly assembled HIV-1 particles (Trono, 1992). These cDNA intermediates and their derivatives may have contributed to the GFP transgene signal in 4-day animals. Moreover, it has been found that unintegrated lentiviral proviral DNA may persist in transduced TE671 (muscle), 293T (kidney), and HepG2 (liver) cells for more than 4-5 passages, but disappear by 40 passages (Chang et al., 1999). Transient GFP expression caused by integrase-defective lentiviral vectors was observed for as much as 10 days in CD34$^+$ cells and 14 days in 293 cells (Haas et al., 2000). No lymphocyte infiltration or other signs of inflammation were observed in any liver or spleen samples from mice 4 days or 40 days after injection in this study, although a transient elevation was observed in serum alanine amino-transferase level by others (Park et al., 2000). Thus, the loss of GFP transgene in the liver is unlikely to be related to the loss of transduced cells resulting from liver toxicity.

One of the most disturbing concerns for gene therapy in humans is the possibility of germline integration of transgene, which might result in the introduction of heritable genetic changes into the offspring of patients (Pilling, 1999). Germline integration may lead to insertional mutations that might have devastating consequences, as indicated in some of the transgenic mice produced by pronuclear microinjection (Woychik et al., 1985; McNeish et al., 1988). To assess the risk of germline integration by a first-generation lentiviral vector, transgene frequency was quantitated in whole gonads of mature mice (Table 3). From undetectable to 9 copies/$10^5$ genome levels of transgene were found in all testes (n=5), and all but one ovary (n=5). A very low level of transgene (3 copies/$10^5$ genomes) was observed in one of the six control animals, although special precautions were taken during perfusion, necropsy, DNA isolation, and QPCR assay. Thus, the possibility of cross-contamination cannot be ruled out. In addition, very high levels of transgene ($2.08 \pm 1.7 \times 10^4$ copies/$10^5$ genomes) detected in the PBL of treated mice may contaminate the gonad if not eliminated completely by perfusion. Even if the transgene found in the gonads is real, the hematopoietic spread of lentiviral vector to spermatocytes or developing oocytes is unlikely because they are relatively inaccessible to large molecules or to infection by viruses (Gordon, 1998). Moreover, there are statistical considerations that mitigate against the germline transfer of foreign DNA that reaches an offspring. For example, integration of transgene into one spermatogenic cell would lead to the genetic transformation of only a few of the millions of cells that would ultimately reach the ejaculate. Also, of the about 400,000 oocytes present in the human ovary at the onset of menstruation, only a few hundred are ovulated during the reproductive lifespan of a woman, and fewer than a dozen of those ovulated oocytes contribute their genes to subsequent offspring. Thus, together with the observations provided herein, the risk of germline transmission of the first-generation lentiviral vector by i.v. administration is very low.

The most surprising observation was that bone marrow exhibited the highest transgene frequency (ranging from 0.21 to 22.7% of total bone-marrow genome) in all mice tested 40 days after injection (Table 3). This was consistent with the observation that high levels of transgene were detected in PBL from these animals (ranging from 0.61 to 62.7%). It was also supported by the results that up to 10% of PBL expressed GFP as determined by FACS analysis. In addition, the transgene levels in PBL decreased significantly from a mean of 0.77% on day 4 to 0.07% on day 11, and then increased considerably back to 0.73% on day 25 and to 20.8% on day 40 following injection. This observation suggested the presence of an additional resource for GFP$^+$ leukocytes, implying the transduction of hematopoietic progenitor cells. This study provides the first indication that bone marrow may be a susceptible target tissue for i.v. administration of VSVG-pseudotyped lentiviral vectors. It is possible that intravenously delivered lentiviral vector may reach stem cells; ex vivo transduction studies have demonstrated the capability of lentiviral vectors to transduce more primitive and quiescent stem cells (Woods, 2001; Case et al., 1999). The i.v. approach may overcome some of the difficulties encountered by ex vivo approaches, such as limited gene transfer efficiency, maintenance of long-term engraftment of the transduced cells, and in vitro manipulation steps (Richter et al., 2001).

Example II

Mucopolysaccharidosis type I (MPS I) is an inborn error of lysosomal glycosaminoglycan (GAG) metabolism resulting from deficiency of alpha-L-iduronidase (IDUA). While allogeneic hematopoietic stem cell (HSC) transplantation results in systemic metabolic correction, including prevention of neurologic damage, attempts to exploit Moloney murine leukemia virus vectors have failed to demonstrate the requisite qualities to merit substitution of ex vivo HSC gene therapy for allogenic HSC transplantation. Lentiviral vectors may integrate into non-dividing cells and may have broad tropism when pseudotyped with VSV-G envelope, thus potentially solving this problem.

A murine model of MPS I (kindly provided by Hong-Hua Li and Elizabeth F. Neufeld; Zheng et al., 2001) was used to evaluate transgene expression in fibroblasts from these mice. Mice were genotyped with a SYBR Green assay from which primary skin fibroblast cultures were established. Second- and third-generation HIV-1 based vectors were generated to transduce these IDUA-deficient murine fibroblasts with either GFP or IDUA. Second generation (three-plasmid) and third generation (four-plasmid) SIN lentiviral vectors were prepared with either GFP (pCS-CG) or IDUA (pCS-P1) transgenes by co-transfection into 293T cells. Potency of 48 hour viral supernatants was assessed by two methods. In the first assay, real-time quantitative PCR was exploited using a primer-probe set for the minus strong-stop cDNA (U5/R region) of encapsulated lentiviral genomes (Scherr et al., 2001) yielding titers between $2 \times 10^6$ genomes/mL and $5 \times 10^7$ genomes/ml. In the second assay, 293T cells were exposed to GFP vector supernatants, and then subjected to FACS analysis to select for transduced cells yielding titers of $1 \times 10^5$ TU/mL. Third-generation vectors were found to be comparable to second-generation preparations.

Murine IDUA-deficient fibroblasts ($2.5 \times 10^5$ cells/plate) were exposed to various concentrations of vector and incubated for 24 hours before changing the media, and then cultured for an additional 6 days prior to analysis. Cells transduced with third generation IDUA (pCS-P1) were found to have markedly increased IDUA enzymatic activity (60-120 nmol/mg/hr) comparable to that of normal human fibroblasts or leukocytes. Quantitative PCR assays for the IDUA and GFP transgenes quantified the level of integration of the transgene within the genome (see Example I). The real-time QPCR assays for the third generation IDUA and GFP vectors found that the average percentage of transduced cells was 60% whereas the negative control was 0%. Microscopy analysis of GFP transduced cells showed similar results.

For in vivo transduction, a transgene plasmid (PCS-P1) containing the human IDUA cDNA sequence under transcriptional control of the human PGK promoter was prepared. Vector preparations were generated by transient cotransfection of 293T cells using a third-generation 4 plasmid packaging system with Rev function (pEFRev) separated from other helper functions (p2NRF) (kindly provided by T. Kafri et al. Real-time quantitative PCR methods were exploited to determine lentiviral particle numbers in vector preparations, and to assess transduction efficiency (Example I).

Figure 2:
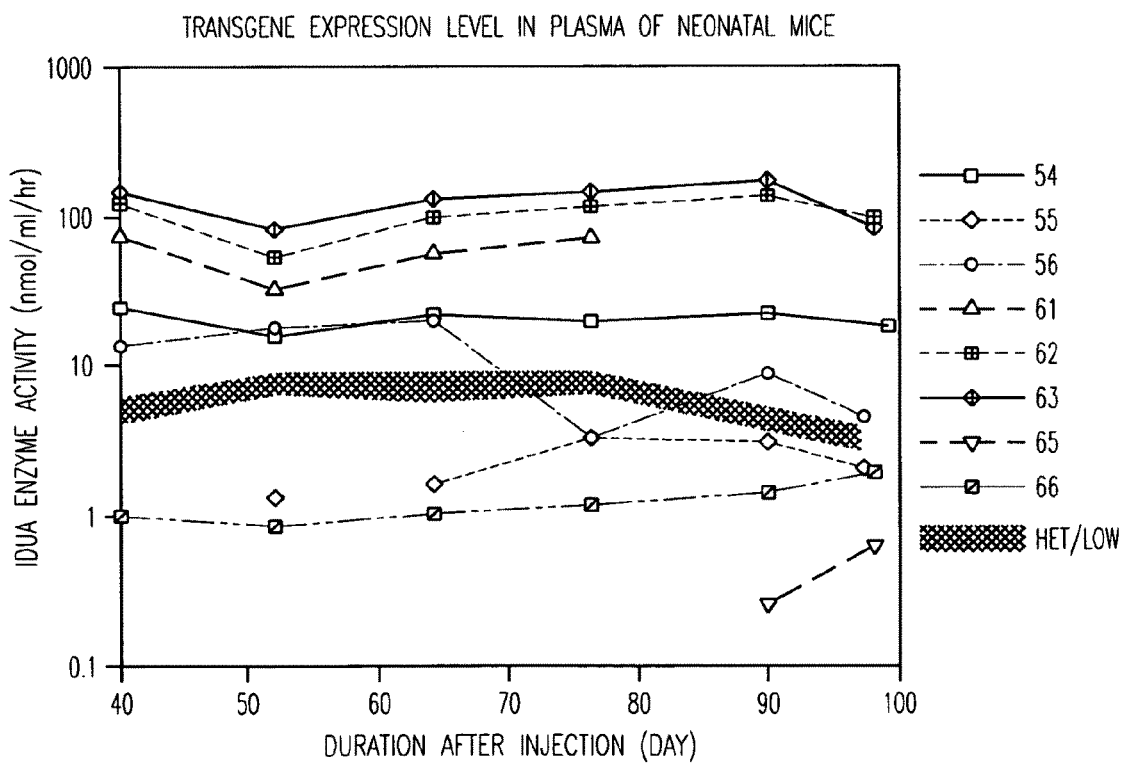
FIG. 2 shows the increase in blood levels of therapeutic IDUA in MPS I mice treated by intravenous administration of an IDUA encoding recombinant lentivirus contrasting the increase in those treated by intravenous administration of a control recombinant lentivirus. The range of activity of IDUA in heterozygous IDUA transgenic mice is shown as a hatched band marked HET/HIGH HET/LOW.

Intravenous injection of an IDUA encoding replication-defective (third generation) VSVG pseudotyped lentiviral vector (e.g., $5 \times 10^7$ TU; FIG. 1) into newborn mice resulted in higher-than-normal levels of alpha-L-iduronidase in blood (FIG. 2). The circulating levels were up to 1-log-fold higher than normal circulating levels, and those levels were much higher than those achieved in efficacious bone marrow transplantation. Further, the circulating levels were up to at least 1-log-fold higher than those achieved by any other means of gene therapy, e.g., intravenous injection of a retrovirus vector in a mouse model of mucopolysaccharidosis type VII (Xu et al., 2002). Moreover, circulating levels of enzyme persisted throughout the period of observation (i.e., 3 months after treatment). Because lentiviral vectors integrate the therapeutic gene into the host chromosome, therapeutic levels of protein (enzyme) are expected to persist for long periods of time, probably for the lifetime of the treated individual.

Figures 3A, 3B, 3C:
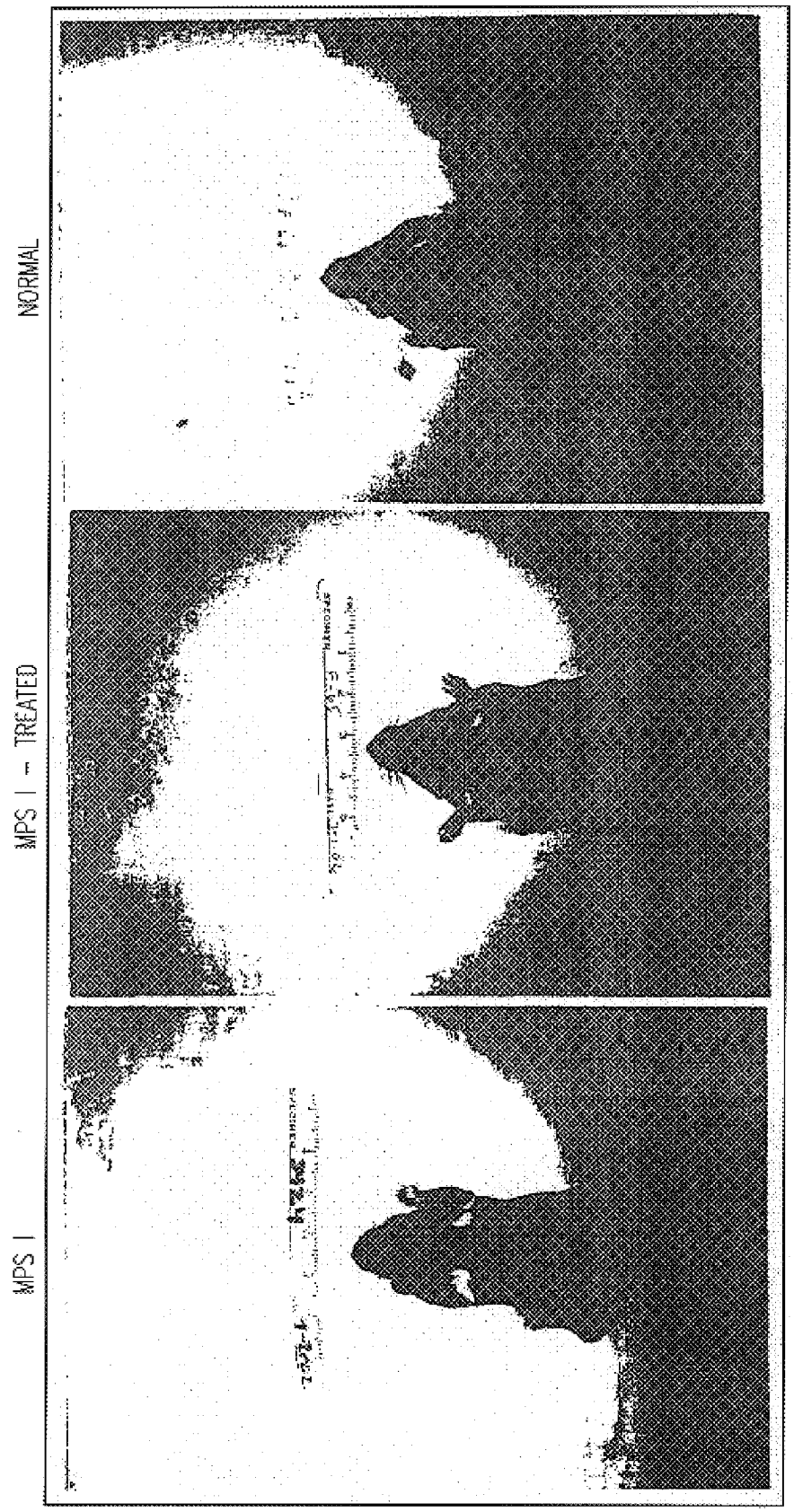
FIG. 3 shows the therapeutic effect of intravenous administration of an IDUA encoding recombinant lentivirus on the facial pathology of a mouse with MPSI.
Figure 4:
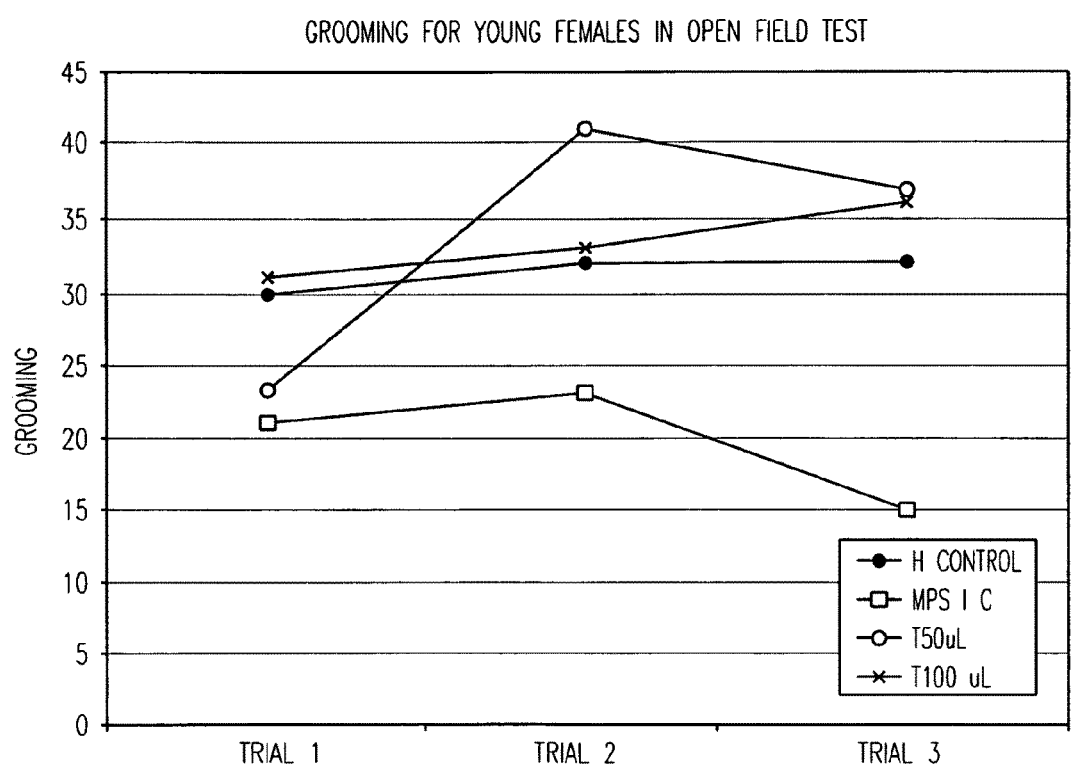
FIG. 4 shows preservation of normal behavior in MPS I mice due to intravenous administration of an IDUA encoding recombinant lentivirus.
Figure 5C:
FIG. 5 illustrates the pathology observed in untreated Hurler syndrome mice (A), normal mice (B), and IDUA lentivirus-treated Hurler syndrome mice (C). The sections were stained with a horseradish peroxidase conjugated anti-alpha-GM2 ganglioside antibody.
Figure 5B:
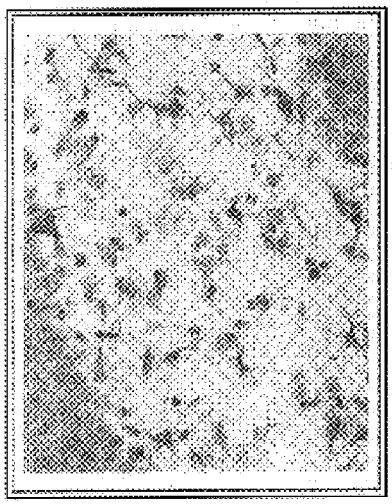
Figure 5A:

In addition, intravenous infusion of newborn MPS I mice with an IDUA encoding recombinant lentivirus resulted in normal facial appearance (FIG. 3) indicating the efficacious effect of transgene expression on bone growth. Further, intravenous infusion of newborn MPS I mice with the IDUA encoding vector also resulted in normal parameters of behavior (FIG. 4) indicating the efficacy of this treatment on the progressive brain degeneration of MPS I. Moreover, FIG. 5 shows a micrograph of the pathology observed in mice with Hurler syndrome as well a micrograph of IDUA lentivirus treated mice which demonstrates that treated mice have a decrease or lack of GM-2 ganglioside pathology.

Example III

Materials and Methods

Plasmids. The plasmid for 5B transposon expression, pT-CAGGS-GUS (transposon), was constructed as follows. A 2.3 kb fragment containing human GUSB cDNA was excised from pHug13 (ATCC 95658) by EcoRI digestion and ligated to EcoRI sites in the poly linker in pCAGGS. The resulting expression cassette for GUSB expression included a cytomegalovirus enhancer, chicken β-actin promoter, the initial intron of the chicken β-actin gene, GUSB cDNA, and a rabbit β-globin and SV40 polyadenylation signal. This expression cassette was inserted between SspI and HindIII sites of the pT/BH transposon polylinker. The SB transposase expression plasmid pCMV-SB10 has been previously described (Ivics, 1997). Pyrogen-free plasmids were used in this study and were isolated using QiaFree kit (Qiagen, City, State).

Mice. MPS VII mutant mice (B6.C-H-2bml/ByBir-gus$^{mps}$) were obtained from Jackson Laboratories (Bar Harbor, Me.) and maintained in the AAALAC-accredited Specific Pathogen-Free mouse facility at the University of Minnesota. Homozygous mutant mice were produced by breeding of heterozygotes. Genotyping was performed by allelic discrimination assay using TaqMan chemistry.

Injections. The plasmids were injected into the tail vein using a 3-cc latex-free syringe with a 271/2G needle. The hydrodynamics-based procedure was performed as described in Wolff et al. (2000). Each mouse received 25-37.5 μg of plasmid DNA in lactated Ringers solution, in a total volume equal to 10% of body weight. One animal from each group died before completion of the experiment: one mouse from Treatment Group I and one mouse from Treatment Group 3 died on 1 week post-injection and one mouse from Treatment Group 2 died 4 weeks post-injection. The organs from these mice were resected within 8 hours of death and used for enzyme quantification and GUSB histochemical staining.

Treatment regimens. In the short-term experiment, four groups of MPS VII or wt mice (n=4 each) received 25 μg of pT/BH-CAGGS-GUS (MPSVII and treatment groups) or pBluescript (MPS VII and wt control groups). The mice were euthanized by CO inhalation 48 hours after injections. 400 μl blood was drawn from the heart for plasma isolation, and livers were extracted and preserved for biochemical molecular, histochemical and pathological analysis.

For the long-experiment, MPS VII mice age 4-26 weeks were used. An aliquot (25 μg) of a single preparation of transposon pT-CAGG5-GUSB was injected either alone (Treatment Group 1), or with pCMV-SB 10 at 1:1 (Treatment Group 2) or 10:1 (Treatment Group 3) molar ratios. The amount of injected DNA was kept the same in each group (37.5 μg) with the filler plasmid, pBluescript. The control group of MPS VII mice was injected with the filler plasmid alone. All injections were performed only once.

The mice were bled by retroorbital phlebotomy 48 hours, 1 week, 2 weeks, and 4 weeks post-injection to obtain plasma for enzyme assays. 8 weeks post-injection, mice were euthanized by $CO_2$ inhalation, and the organs (liver, spleen, heart kidney, lung, brain, and gonads) were resected, cut into 2 mm$^3$ sections and preserved in different ways for analysis. Prior to organ resection, 400 ml of blood was drawn for plasma and white blood cell (WBC) isolation.

For lysosomal enzyme quantification, plasma and tissues were snap-frozen in liquid nitrogen and stored at −80° C. Activities of GUSB, alpha-galactosidase and total β-hexosaminidase were measured in tissue homogenates and plasma using fluorometric assay. Protein concentrations were determined with Bradford assay (Bradford, 1976) using Bio-Rad reagent.

For histology and histopathology studies, tissues were fixed in 10% neutral-buffered formalin, embedded in paraffin and sectioned at 6 μm for staining with Hematoxylin and Eosin.

Histochemical localization of GUSB was performed in 6-8 μm frozen sections stored at −80° C. using AS-BI-naphthol-β-D-glucuronic acid (Sigma) as described in Wolfe and Sands (2000) and Ghodsi et al. (1998).

For detection of storage vacuoles, tissues were fixed in 2.5% glutaraldehyde in 0.1 N cacodylate buffer for at least 48 hours at 4° C. Tissues were embedded in Epon 812 resin (Electron Microscopy Sciences, Ft. Washington, Pa.). Sections (0.5 μm) were prepared and stained with toluidine blue as described in Wolfe and Sands (2000).

Results

Figure 6:
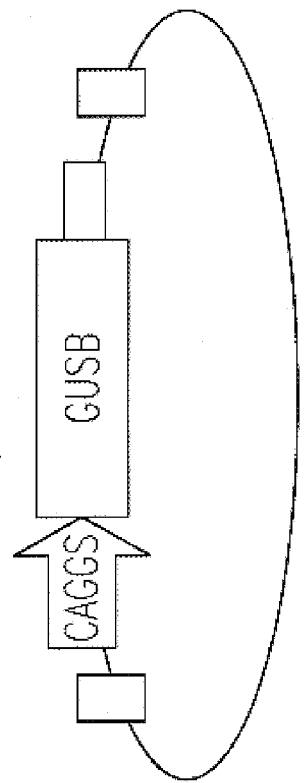
FIG. 6 shows a schematic of pT-CAGGS-GUSB.

The transposon plasmid carried human GUSB cDNA regulated by a strong promoter (FIG. 6) which expressed very high levels of f-glucuronidase. Correct assembly of pT-CAGG5-GUSB was validated by restriction enzyme analysis, and the structure of GUSB was confirmed by sequencing (data not shown). GUSB expression was confirmed by transfection of primary β-glucuronidase-deficient murine fibroblasts. To determine whether beta-glucuronidase can be detected in plasma 48 hours after hydrodynamic infusion of adult MPS VII mice and wild-type mice. Mice at 8-12 weeks of age were injected with 25 µg of either pT-CAGG5-GUS plasmid or pBluescript. All mice tolerated the procedure well with only one death of a wild-type mouse.

Figure 7:
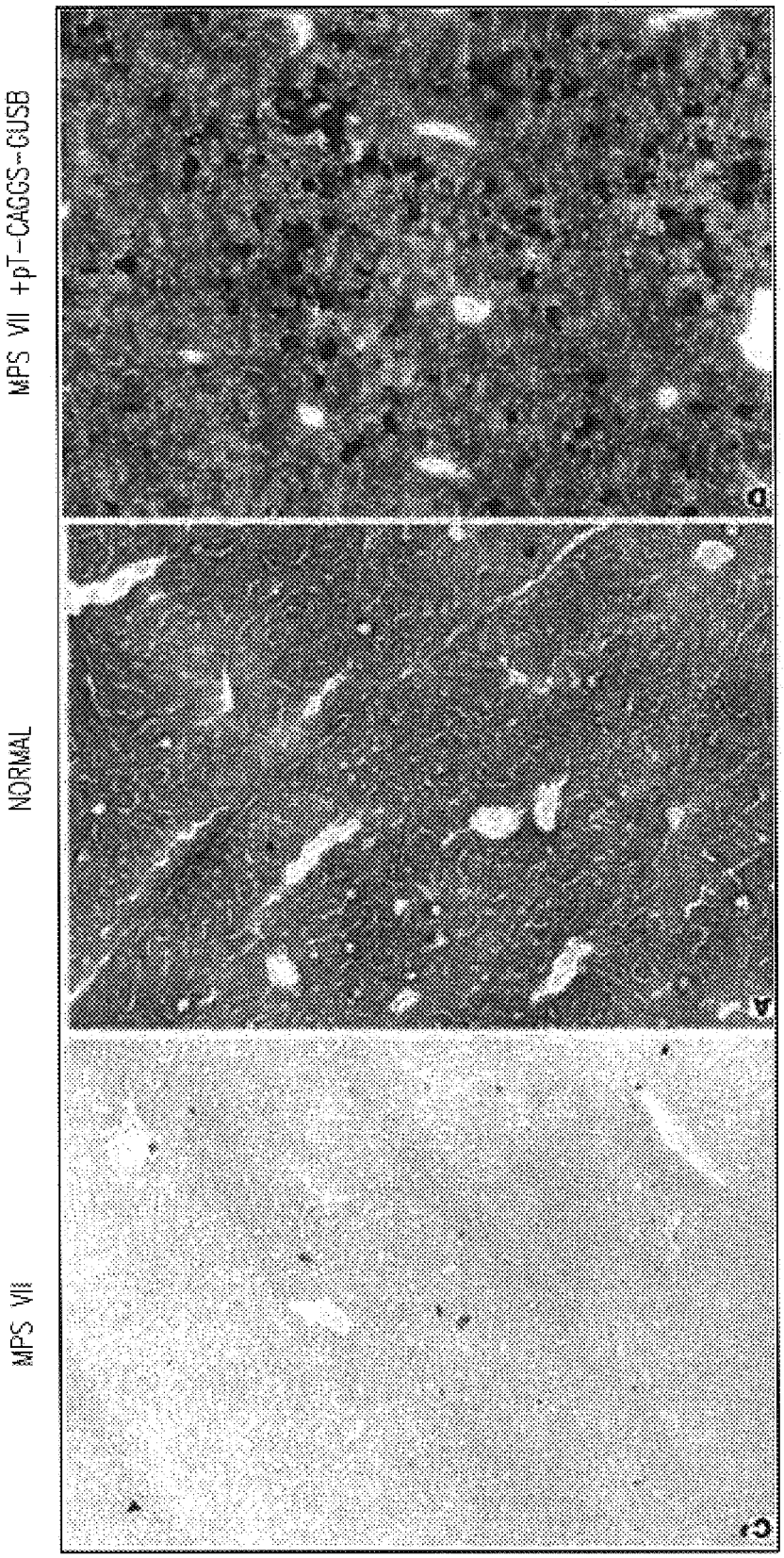
FIG. 7 shows histochemical visualization of beta-glucuronidase catalytic activity in liver 48 hours after hydrodynamic infusion of pT-CAGGS-GUSB plasmid. Transfected cells stain intensively red. A) Untreated MPS VII mouse. B) Wild-type mouse showing normal levels of beta-glucuronidase activity. C) MPS VII mouse treated with pT-CAGGS-GUSB only. Dark red punctate spots are likely transfected cells expressing extremely high levels of beta-glucuronidase enzyme while more diffusely red cells have taken up enzyme by mannose-6-phosphate receptor-mediated endocytosis. (Representative views of 6 micron sections at 10× magnification.)

The plasmid pT-CAGGS-GUS mediated high levels β-glucuronidase expression in the liver after hydrodynamic infusion. In GUS-deficient mice, as well as in wild-type mice, foci of intensively bright red staining were evenly distributed in liver tissue (FIG. 7). Counterstaining with methyl green permitted localization GUSB activity to hepatocytes (predominantly) and Kupffer cells. Varying degrees of staining were observed in all cells, suggesting enzyme cross-correction. Beta-glucuronidase activity (Table 4) in treated MPS VII animals exceeded that in untreated wild-type mice by over 10-fold.

Group 2) and 10:1 transposon to transposase plasmid (Treatment Group 3). All treated mice received an equal amount of 25 µg of pT/BH-CAGGS-GUS. The injected DNA amount was kept equal in all mice by using pBluescript as the filler plasmid. MPS VII mice from the negative control group received pBluescript alone. Forty-eight hours after injection, β-glucuronidase activities in the plasma of treated animals were equally high in all three surviving animals and in the same range as those in the short-term experiment (Table 5). One week post-injection, plasma β-glucuronidase in mice from Treatment Group 1 was reduced to 71.8% of initial 48 hour post injection activity. In Treatment Groups 2 and 3, enzymatic activity had decreased to 37.3% and 28.6% of initial activity, respectively. At one month, β-glucuronidase in plasma was virtually undetectable in all three groups. Secondary elevations of other lysosomal enzymes concomitant

TABLE 4

Beta-glucuronidase Enzyme Activity in Plasma and Liver 48-hours after Hydrodynamic Infusion of pT-CAGGS-GUSB plasmid.

| MICE §Gen | Injection | | | | Enzyme activities* | | | | |
|---|---|---|---|---|---|---|---|---|---|
| | Weight | Vol. | Time | GUS Quality** | GUS Liver | GUS Plasma | hexosaminidase Liver | hexosaminidase Plasma | galactosidase Liver |
| PT/CAGGS-GUS, 25 µg | | | | | | | | | |
| MPSVII 1 M | 25.0 g | 2.5 ml | 10 seconds | Excellent | 2,552 | 5,209 | 4,300 | 5890 | 124 |
| MPSVII 2 M | 24.7 g | 2.5 ml | 12 seconds | Good | 1,860 | 2,715 | 4,386 | N/A | 132 |
| MPSVII 3 M | 22.9 g | 2.3 ml | 19 seconds | Poor | 99 | 3 | 5,185 | 1,229 | 123 |
| MPSVII 4 F | 19.0 g | 1.9 ml | 12 seconds | Fair | 2 | 2 | 6,561 | 8,107 | 123 |
| Unaffected 5 F | 20.3 g | 2.0 ml | 10 seconds | Good | 75 | 119 | 936 | 953 | 49 |
| Unaffected 6 M | 30.6 g | 3.0 ml | 14 seconds | Fair | 16 | 123 | 675 | 611 | 43 |
| Unaffected 7∞F | 19.9 g | 2.0 ml | 10 seconds | Excellent | 314 | 297 | 911 | 453 | 49 |
| Unaffected 8 M | 26.8 g | 2.7 ml | 9 seconds | Excellent | Died within 1 hour post injection | | | | |
| pBluescript, 25 µg | | | | | | | | | |
| MPSVII 9 F | 20.4 g | 2.0 ml | Injection failed, mouse survived but was not used further | | | | | | |
| MPSVII 10 F | 17.7 g | 1.8 ml | 10 seconds | Excellent | 1 | 2 | 6,786 | 1,365 | 130 |
| MPSVII 11 F | 21.4 g | 2.1 ml | 8 seconds | Excellent | 1 | 1 | 6,526 | 4,750 | 153 |
| MPSVII 12 F | 20.0 g | 2.0 ml | 8 seconds | Excellent | 1 | 2 | 7,634 | 1,520 | 179 |
| Unaffected 13 M | 28.6 g | 2.9 ml | 15 seconds | Poor | 118 | 7 | 696 | 491 | 42 |
| Unaffected 14 F | 28.0 g | 2.8 ml | 9 seconds | Excellent | 9 | 9 | 1,187 | 792 | 75 |
| Unaffected 15 F | 22.9 g | 2.3 ml | 12 seconds | Poor | 86 | 9 | 845 | 633 | 38 |
| Unaffected 16 F | 22.8 g | 2.3 ml | 9 seconds | Excellent | 94 | 12 | 1,031 | 649 | 37 |
| Untreated | | | | | | | | | |
| MPSVII 17 M | — | — | — | — | 1 | 1.7 | 5,210 | 1,365 | 125 |
| MPSVII 18 F | — | — | — | — | 1.3 | 1.4 | 7,231 | 2,679 | 148 |
| MPSVII 19 F | — | — | — | — | 1.1 | 1.9 | 6,718 | 1,868 | 130 |
| Unaffected 20 F | — | — | — | — | 87 | 14 | 985 | 675 | 44 |
| Unaffected 21 F | — | — | — | — | 84 | 9.6 | 1,004 | ? | ? |
| Unaffected 22 F | — | — | — | — | 188 | 15 | 685 | 589 | 42 |

*Enzyme activity is expressed as nmoles of 4 MU/mg protein/h for liver and as nmoles of 4 MU/ml plasma/h for plasma
§Gen stands for gender and genotype
**Time and Quality refer to the microinjection time and apparent success at the time of injection
∞This mouse is a replacement for an unaffected mouse, in which injection failed (the needle did not go into the vein)

β-glucuronidase activity was easily detectable in plasma (Table 4), and may be used as a presumptive indicator of the presence/absence of pT-CAGGS-GUSB. This proved to be a convenient method of monitoring the success of the procedure for administering the test agent.

Eight-week β-glucuronidase enzyme activity in plasma after co-injection with SB plasmid. MPS VII mice were either injected with pT/CAGGS-GUSB alone (Treatment Group 1) or co-injected with pCMV-SB10 at two different molar ratios of the transposon to transposase plasmid: 1:1 (Treatment with the deficiency of the causative enzyme have been observed in storage diseases and respond to treatment. In this series of mice, hexosaminidase levels in untreated mice were found to be pathologically elevated. At time point 1 week, hexosaminidase levels in plasma decreased to 78.5% in Treatment Group 1; 58.5% in Treatment Group 2; and 61.8% in Treatment Group 3 as compared to time-point 2 days post-injection. No reduction of hexosaminidase activity was observed in sham-treated MPS VII mice. At a later time point (time point, weeks/hours), levels remained/changed (Table 5).

TABLE 5

Beta-glucuronidase Activity in Plasma 2 and 7 days after co-injection by hydrodynamic infusion of pT-CAGGS-GUS plasmid

| Mouse | 2 Days | 7 Days | % initial Activity | 2 days | 7 days | % Initial Activity |
|---|---|---|---|---|---|---|
| | | | | HEX in plasma, nmole/ml/hr | | |
| pT/CAGGS_GUS | | | | | | |
| 1 | 5304 | 3855 | 72.7 | 3,300 | 2160 | 65.5 |
| 3 | 3602 | 2114 | 58.7 | 3492 | 1980 | 56.7 |
| 4 | 2002 | 1868 | 93.3 | 2211 | | 113.4 |
| Mean | 3636 ± 1651 | 2612 ± 1083 | 74.9 ± 17.4%, n = 3 | 3001 ± 691 | 2216 ± 268 | |
| pT/CAGGS-GUSB + pSB10 1:1 | | | | | | |
| 5 | 2692 | 566 | 21 | 3491 | 2132 | 61.1 |
| 6 | 3800 | 823 | 21.7 | 6600 | 2165 | 32.8 |
| 7 | 6405 | 2074 | 32.4 | 2376 | 2039 | 85.8 |
| 8 | 3119 | 1116 | 35.8 | 3432 | 1855 | 54.1 |
| Mean | 4004 | 1145 | 28.6%, n = 4 | 3975 | 2048 | 58.5 |
| pTCAGGS-GUSB plus pSB10, 10:1 | | | | | | |
| 9 | 7711 | 2565 | 33.3 | 2343 | 1835 | 78.3 |
| 10 | 3372 | 1172 | 34.8 | 2970 | 1835 | 61.8 |
| 11 | 0 | 0 | | 7946 | 3610 | 45.4 |
| 12 | 1552 | 982 | 63.3 | 3928 | N/A | |
| Mean | 4212 | 1573 | 37.3%, n = 3 | 4420 | 2427 | 61.8 |
| pBluescript | | | | | | |
| 13 | Neg. control | 0 | | 2897 | 3274 | 113 |
| 14 | Neg. control | 0 | | 3815 | N/A | |
| Wild-type 6.9-14.9 (n = 6) Untreated | | | | | | |

Figure 8:
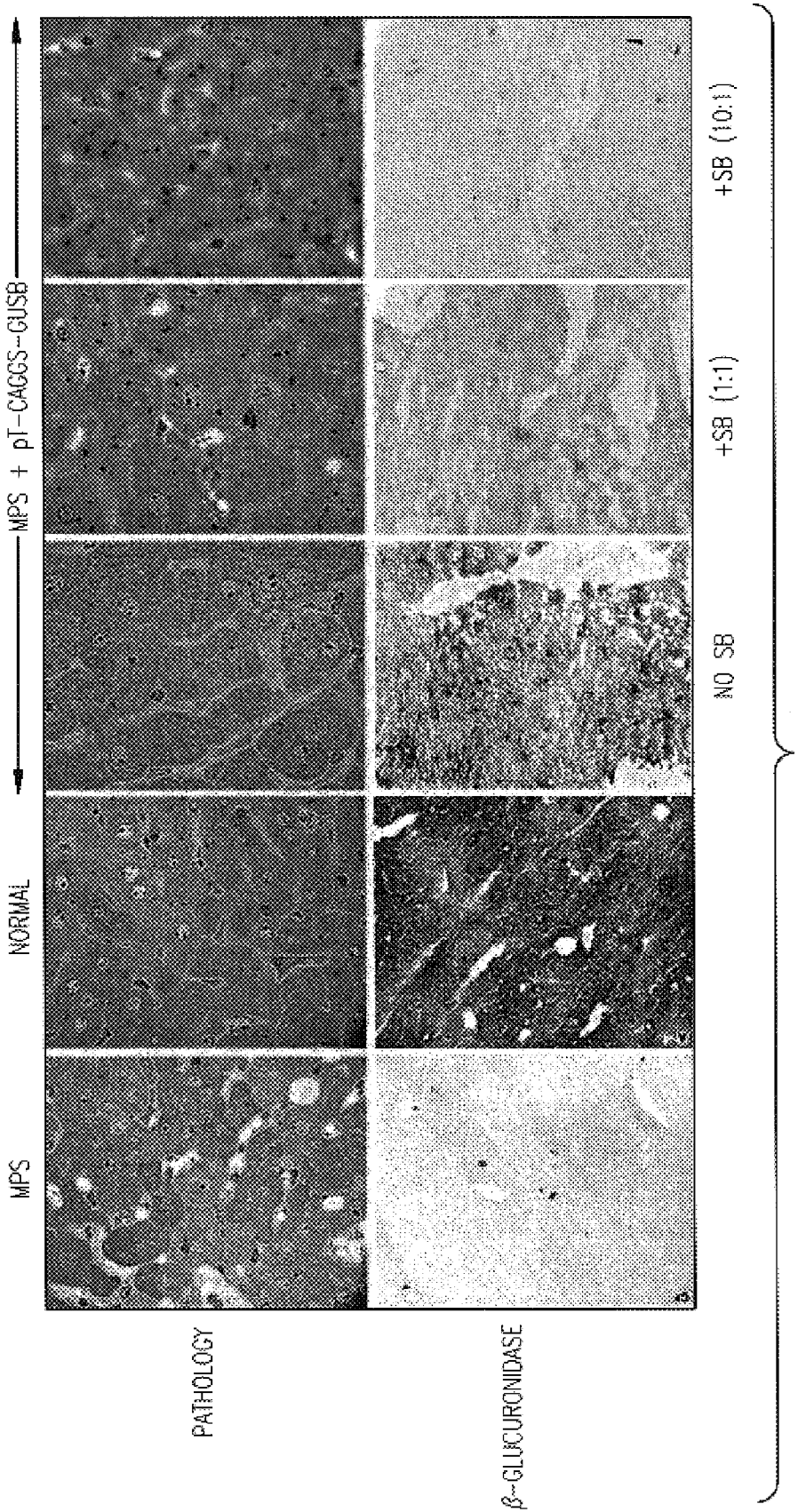
FIG. 8 shows data from two months after intravenous infusion of pT-CAGSS-GUSB plasmid. Liver sections are stained for beta-glucuronidase activity (left) and with toluidine blue to visualize pathologic lysosomal vacuolization (right). A) and B) are MPS VII mouse untreated. C) and D) are wild-type mouse, untreated. E) and F) are MPS VII mouse treated with pT-CAGGS-GUSB alone. G) and H) are MPS VII mouse treated by co-injection of pT-CAGGS-GUSB and pSB plasmids in equal amounts, a 1:1 ratio. I) and J) represent an MPS VII mouse treated by co-injection of pT-CAGGS-GUSB and pSB plasmids in a ratio of 10:1.
Figure 9:
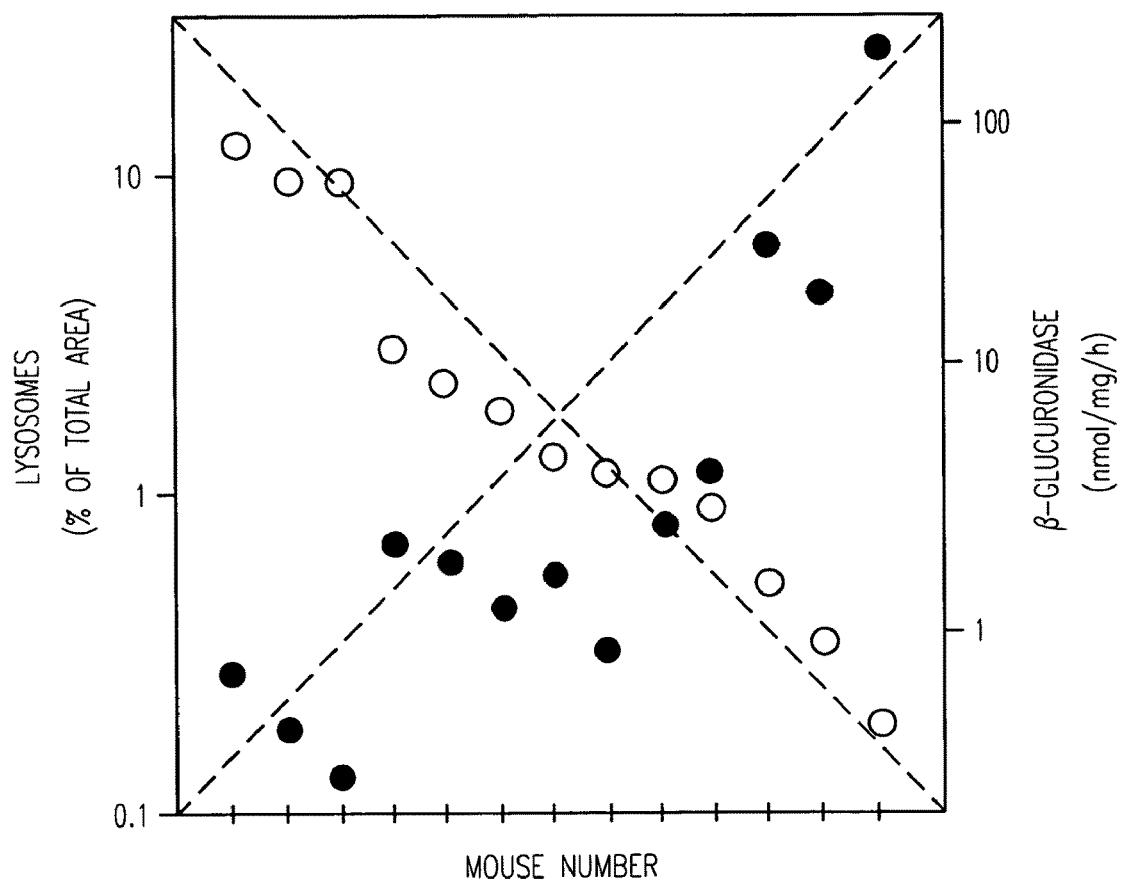
FIG. 9 provides data from mice studied at 2 months after treatment. There is a dose-related correspondence of hepatic lysosomal pathology (area of vacuolization) to the level of hepatic beta-glucuronidase enzyme activity Mice receiving pT-CAGGS-GUSB demonstrated high levels of enzyme activity and complete clearance of lysosomal pathology, while those co-injected with pT-CAGGS-GUSB and pSB showed intermediate levels of response.

Eight-week enzyme levels in organs. Two months after administration of pTCAGGS-GUSB transposon, beta-glucuronidase persisted in liver and spleen in all three groups and the levels of β-glucurorudase in animals that did not receive transposase were higher than in those that were co-injected with the transposase plasmid. Histochemical staining revealed considerable reduction of positively stained cells both in liver and in spleen (FIG. 8). Fluorometric quantification of β-glucuronidase activity showed that in Treatment Group 1 it was approximately 8-fold higher than in either group 1 or 2 (Table 7).

TABLE 6

Beta-glucuronidase activity in MPS VII mouse organs 1 week and 1 month after injection, nmol/mg protein/hr

| Organ/Mouse | #2 (No SB) | #14 (SB1:10) | #8 (SB1:1) | W.T. |
|---|---|---|---|---|
| Liver | 5184 | 6185 | 28 | 119-188 n = 6 |
| Spleen | 6080 | 4534 | 3.9 | 269-290 n = 3 |
| Heart | 98 | 94 | 2.1 | 10-13 n = 3 |
| Kidney | 59 | 59 | 1.9 | 60-74 n = 3 |
| Lung | 49 | 65 | 1.8 | 60-83 n = 3 |
| Gonad | N/A (testis) | N/A (testis) | 0 (ovary) | 223 n = 1 |
| Brain | N/A | N/A | 0 | 17-20 n = 3 |

TABLE 7

GUSB activity in liver and spleen 8 weeks post-injection, nmol/mg/hr

| Treatment Group | Transposon pT-CAGGS-GUSB (mcg) | Transposase pCMV-SB10 (mcg) | Inert DNA pBluescript (mcg) | Mouse | β-glucuronidase | |
|---|---|---|---|---|---|---|
| | | | | | Liver (nmol/mg/h) | Spleen (nmol/mg/h) |
| Transposon Alone | 25 | 0 | 12.5 | 1 | 29.5 | 2.1 |
| | | | | 3 | 18.6 | 3.2 |
| | | | | 4 | 2.4 | 1.04 |
| Transposon:Transposase 1:1 | 25 | 12.5 | 0 | 6 | 1.15 | 0.59 |
| | | | | 9 | 2.21 | 1.0 |
| | | | | 10 | 1.92 | 0.85 |
| Transposon:Transposase 10:1 | 25 | 1.25 | 11.25 | 11 | 4.01 | 0.82 |
| | | | | 12 | 1.51 | 0.89 |
| | | | | 15 | 0.78 | 2.71 |

TABLE 7-continued

GUSB activity in liver and spleen 8 weeks post-injection, nmol/mg/hr

| Treatment Group | Transposon pT-CAGGS-GUSB (mcg) | Transposase pCMV-SB10 (mcg) | Inert DNA pBluescript (mcg) | Mouse | β-glucuronidase Liver (nmol/mg/h) | β-glucuronidase Spleen (nmol/mg/h) |
|---|---|---|---|---|---|---|
| Control (−) | 0 | 0 | 37.5 | 17 | 0.63 | 0.76 |
|  |  |  |  | 33 | 0.39 | 0.75 |
| Control (+) |  |  | Untreated | 166.8; | (119-188), n = 6 | 368; 269-290, n = 3 |

Distribution of β-glucuronidase expression in various mouse organs was studied at one week (1 mouse from Treatment Group 1 and Treatment group 3), 4 weeks (1 mouse from Treatment Group 2) (Table 6) and 8 weeks (n=3 from each group) (Table 4). This study showed that during the first week following hydrodynamic-based administration, β-glucuronidase activities in liver and spleen were comparably high; the heart had levels less than 2% that of liver and spleen. Moreover, the lung had less than 1%, and the ovary had undetectable, β-glucuronidase activity.

Extent of correction of the pathology. No lesions were seen in Hematoxylin and Eosin-stained 6 mm sections of liver, spleen, lung, testis, ovary, gut, cerebellum, kidney and heart from treated, sham-treated or untreated MPS mutant mice. Toluidene-blue staining of 0.5 mm sections of liver and spleen revealed a dramatic reduction in the number and size of storage vacuoles in all treated groups (FIG. 8). In Treatment Group 1, where the sections were indistinguishable from those of normal controls, loss of storage vacuoles appeared complete. Partial reduction of storage was observed in Treatment Groups 2 and 3. Remarkably, storage vacuoles appeared to be not just prevented but actually eliminated in some mice (e.g., mouse #3 was 215 days of age when killed but had no vacuoles; the wt untreated control had many vacuoles at 50 days of age. If treatment of #3 started after it was 50 days of age, the data suggests that vacuoles were not just prevented, but actually eliminated).

Discussion

Therapeutic gene transfer and expression is widely held to require some extraneous mechanism(s) for molecular stabilization and for transmission across the tissue and cellular membranes. Thus, the most feasible forms of gene therapy have used extensively modified replication-defective viral vectors, liposomes or even ex vivo electroporation of DNA into cells prior to transplantation.

While studying a potential means of intravenous injection of unmodified DNA into mice, surprisingly it was found that hydrodynamic administration of a particular plasmid structure was capable of long-term expression with high levels of enzyme expression, achieving a potentially curative response, in a murine model of mucopolysaccharidosis type VII. In particular, expression of the GUSB transgene was easily detected in plasma. Notably, plasma levels of glucuronidase were exceedingly high 1 week post-injection, but became barely detectable after 1 month. This suggests that such transient expression was due to episomal delivery, and that the majority of pT-CAGGS-GUSB plasmid did not persist in an integrated form. By 8 weeks post-injection, β-glucuronidase activity was undetectable in plasma; however, glucuronidase activity was detectable in the liver and spleen. Beta-glucuronidase activity in two out of three mice in Treatment Group 1 was over 10% that of wt, whereas in Treatment Groups 2 and 3 these levels were around 1% that of normal values. The levels observed were sufficient to result in the first successful treatment of a metabolic disease by intravenous injection of a plasmid.

Further, the results show there was a "dose effect", with levels of expression corresponding to the level of reversal of pathology. These levels of expression were sufficient to reverse accumulation of GAG.

As observed by the correlation of glucuronidase enzyme activity to correction (e.g., FIGS. 7 and 8, and Table 7), increases in enzyme activity in the liver corresponded to the degree of metabolic correction. Animals that had the highest level of glucuronidase activity 8 weeks after treatment were clear of pathologic lysosomal accumulations. In these animals, there appears to be a cure of metabolic disease. By extension to the work of enzyme replacement in this same animal model (Sands et al., 1997), this would correspond to a cure of the murine MPS VII phenotype in other studies, especially using non-viral gene transfer systems.

The remarkable aspect of the reported study is the apparent ability to cure this storage disease with out the necessity of using a viral vector. This is the first time a long-term effect has resulted from naked DNA gene therapy (i.e., without the benefit of a viral vector).

Interestingly, beta-glucuronidase levels were lower when transposase was present. For example, eight-weeks after pT-CAGGS-GU5B administration, glucuronidase expression in Treatment Group 1 was higher than in any ($p<0.01$) or all ($p<0.01$) of the others (Treatment Group 2 and Treatment Group 3). This difference was not random, but was statistically significant. Notably, mice Treatment Group 2 and Treatment Group 3 received the same amount of pT-CAGGS-GUSB, but showed much lower levels of glucuronidase expression ($p<0.01$). From this observation, SB transposase may be responsible for these lower levels.

Based on these observations, it is likely that expression of glucuronidase activity is predominantly from an episomal form. Nevertheless, it appears that episomal gene expression by this means has the potential for effecting a long-term treatment.

TABLE 8

Dose effect of β-glucuronidase activity on storage clearance

| Mb | Treatment Group | 2-Day Glucuronidase Activity | 8-Week Glucuronidase Activity Liver | 8-Week Glucuronidase Activity Spleen | Liver Vacuole Area | Spleen Vacuole Area |
|---|---|---|---|---|---|---|
| 34 | W.T. | 14 | 166.8 | 368 | 0.18 | 0.09 |
| 1 | pT- | 5304 | 29.5 | 2.1 | 0.75 | 2.19 |
| 3 | CAGGS- | 3602 | 18.6 | 3.2 | 0.35 | 2.75 |
| 4 | GUSB | 2002 | 2.4 | 1.04 | 1.11 | 1.76 |
| 6 | pT- | 2692 | 1.15 | 0.59 | 2.02 | 2.83 |
| 9 | CAGGS- | 6405 | 2.21 | 1.0 | 3.13 | 3.35 |
| 10 | GUSB + pCMV-SB10, 1:1 | 3119 | 1.92 | 0.85 | 2.36 | 1.93 |
| 11 | pT- | 7711 | 4.01 | 0.82 | 1.03 | 1.83 |
| 12 | CAGGS- | 3372 | 1.51 | 0.89 | 1.55 | 6.15 |
| 15 | GUS + pCMV-SB10, 10:1 | 1552 | 0.78 | 2.71 | 1.32 | 4.69 |
| 13 | Fail Treatment | 0 | 0.26 | 0.52 | 9.13 | 11.85 |
| 17 | Sham-treated MPS | 0 | 0.63 | 0.76 | 13.65 | N/A |
| 33 | Untreated MPS | 0 | .039 | 0.75 | 9.54 | 6.97 |

REFERENCES

Albritton et al., *Cell*, 57:659 (1989).
Amado et al., *Science*, 285:674 (1999).
Banerji et al., *Cell*, 33:729 (1983).
Barranger et al., *Japanese J. of Inher. Met. Disease*, 51:45 (1989).
Becker et al., *Hum. Gene Ther.*, 10:2559 (1999).
Blomer et al., *J. Virol.*, 71:6641 (1997).
Boshart et al., *Cell* 41:521 (1985).
Burns et al., *Proc. Natl. Acad. Sci. USA*, 90:8033 (1993).
Byrne et al., *Proc. Natl. Acad. Sci. U.S.A.*, 86:5473 (1989).
Calame et al., *Adv. Immunol.* 43:235 (1988).
Campes et al., *Genes Dev.*, 3:537 (1989).
Carlesso et al., *Oncogene*, 9:149 (1994).
Case et al., *Proc. Natl. Acad. Sci. USA*, 96:2988 (1999).
Cech, *J. Amer. Med Assn.*, 260:3030 (1988).
Chang et al., *Gene Ther.* 6:715 (1999).
Coll, *Arch. Virol.*, 140:827 (1995).
Costello et al., *Gene Ther.*, 7:596 (2000).
Douglas et al., *Hum. Gene Ther.*, 10:935 (1999).
Dull et al., *J. Virol.*, 72:8463 (1998).
Edlunch et al., *Science*, 230:912 (1985).
Erickson et al., *J. Biol. Chem.*, 260:14319 (1985).
Fields et al., *New Engl. J. Med.*, 277:989 (1967).
Firon et al., *Am. J. Hum. Genet.*, 46:527 (1990).
Food and Drug Administration (1991) http://www.fda.gov/cber/gdlns/ptcsomat.pdf.
Food and Drug Administration (1998) http://www.fda.gov/cber/gdlns/somgene.pdf.
Furbish et al., *Biochem. Biophys. Acta.* 673:425 (1981).
Ghidsi et al., *Hum. Gene Ther.*, 9:2331 (1998).
Goldman et al., *Hum. Gene Ther.*, 8:2261 (1997).
Gordon, *Mol. Med. Today*, 4:468 (1998).
Gosse et al., *Proc. Natl. Acad. Sci.*, 89:5547 (1992).
Grosveld et al., *Cell*, 51:975 (1987).
Haas et al., *Mol. Ther.* 2:71 (2000).
Hackett et al., WO98/40510
Heid et al., *Genome Res.* 6:986 (1996).
Helene, *Anticancer Drug Dis.*, 6(6):569 (1991.
Ho et al., *Proc. Natl. Acad. Sci. USA*, 68:2810 (1971).
Ivics et al., *Cell*, 91:501 (1997).
Johnson et al., *Gene Ther.*, 7:568 (2000).
Kafri et al., *J. Virol.*, 73:576 (1999).
Kafri et al., *Nat. Genet.*, 17:314 (1997).
Kessel et al., *Science*, 249:374 (1990).
Kim et al., *J. Virol.*, 72:811 (1998).
Konieczko et al., *J. Virol.*, 199:200 (1994).
Lever, *Curr. Opin. Mol. Ther.*, 2:488 (2000).
Marcus-Sakura, *Anal. Biochem.*, 172:289 (1988).
Maher et al., *Antisense Res and Dev.*, 1:227 (1991)
Marthas et al., J. Virol., 67:6047 (1993)
Mastromarino et al., *J. Gen. Virol.*, 68:2359 (1987).
McKnight et al., *Cell*, 37:253 (1984).
McNeish et al., *Science*, 241:837 (1988).
Methods of Enzymology 65:499 (1980).
Miyoshi et al., *J. Virol.*, 72:8150 (1998).
Miyoshi et al., *Proc. Natl. Acad. Sci. USA*, 94:10319 (1997).
Miyoshi et al., *Science*, 283:682 (1999).
Naldini et al., *Proc. Natl. Acad. Sci. USA*, 93:11382 (1996).
Naldini et al., *Science*, 272:263 (1996).
Neural Grafting in the Mammalian CNS, Bjorklund & Stenevi, eds. (1985).
Ng et al., *Mol. Cell Biol.*, 5:2720 (1985).
O'Brian et al., *Science*, 241:1098 (1988).
Orlando et al., *Clin. Chem. Lab. Med.*, 36:255 (1998).
Ory et al., *Proc. Natl. Acad. Sci.*, 93:11400 (1996).
Pan et al., *Mol. Ther.* 6:19 (2002).
Park et al., *Nat. Genet.*, 24:49 (2000).
Pilaro et al., *Toxicol. Pathol.*, 27:4 (1999).
Pilling, *Toxicol. Pathol.*, 27:678 (1999).
Pinkert et al., *Genes Dev.*, 1:268 (1987).
Podsakoff, *Mol. Ther.*, 4:282 (2001).
Poeschla et al., *Nat. Med.*, 4:354 (1998).
Queen and Blatimore, *Cell*, 33:741 (1983).
Rappeport et al., Birth Defects: Original Article Series 22,1:101 (1986).
Reiser et al., *Proc. Natl. Acad. Sci. USA*, 93:15266 (1996).
Richter et al., *Int. J. Hematol.*, 73:162 (2001).

Romano et al., *Stem Cells*, 18:19 (2000).
Sambrook et al., in Molecular Cloning: A Laboratory Manual, Cold Spring Harbor Laboratory, N.Y. (1989).
Sands et al., *Neuro. Dis.*, 7:352 (1997)
Sandhoff et al., In: The Metabolic Basis of Inherited Disease, Scriver et al. (eds), McGraw-Hill, NY, pp. 1807-1839 (1989).
Sattentau et al., *Science*, 234:1120 (1986).
Scherr et al., *BioTechniques*, 31:520 (2001).
Schnitzlein et al., *J. Virol.*, 142:426 (1985).
Schroers et al., *Mol. Ther.*, 1:171 (2000).
Takasaki et al., *J. Biol. Chem.*, 259:10112 (1984).
Trono., *J. Virol.*, 66:4893 (1992).
Tsuji et al., *Proc. Natl. Acad. Sci. USA*, 85:2349 (1988).
Verdier et al., *Toxicol. Sci.*, 47:9 (1999).
Weintraub, *Sci. Am.*, 262:40 (1990).
Whitley et al., *Birth Defects*, 22:7 (1986).
Winoto et al., *EMBO J.* 8:729 (1989).
Wolff et al., *Mol. Thera.* 2:552 (2000).
Woychik et al., *Nature*, 318:36 (1985).
Woods et al., *J. Intern. Med.*, 249:339 (2001).
Xu et al., *Mol. Ther.*, 5:141 (2002).
Zhang et al., *Human Gene Therapy*, 10:1735 (1999).
Zheng et al., *Am. J. Hum. Genet.*, 69:679 (2001).
Zufferey et al., *Nat. Biotech*, 15:871 (1997).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to prevent or inhibit a disorder characterized by the absence or reduced levels of a alpha-L-iduronidase in a mammal, comprising:

administering to a vascular compartment of a mammal having or at risk of the disorder, an effective amount of a recombinant lentivirus comprising a nucleic acid segment encoding alpha-L-iduronidase.

2. The method of claim 1 wherein the recombinant lentivirus comprises a heterologous promoter operably linked to the nucleic acid segment.

3. The method of claim 1 wherein vascular compartment is a vein, artery, bone marrow cavity, heart, spleen, umbilical cord vessel or placenta.

4. The method of claim 1 wherein the mammal is a human.

5. The method of claim 1 wherein the recombinant lentivirus is a pseudotyped virus.

6. The method of claim 5 wherein the pseudotyped lentivirus comprises VSV-G.

7. The method of claim 1 wherein the lentivirus is a human immunodeficiency virus-1 (HIV-1).

8. The method of claim 1 wherein the mammal is a newborn.

9. The method of claim 1 wherein the lentivirus is intravenously administered.

10. The method of claim 8 wherein the lentivirus is administered to a newborn.

* * * * *

UNITED STATES PATENT AND TRADEMARK OFFICE
CERTIFICATE OF CORRECTION

PATENT NO.       : 7,592,321 B2
APPLICATION NO.  : 11/057410
DATED            : September 22, 2009
INVENTOR(S)      : Whitley et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this

Twenty-first Day of September, 2010

David J. Kappos
*Director of the United States Patent and Trademark Office*